US012427285B2

(12) United States Patent
Blanchard et al.

(10) Patent No.: US 12,427,285 B2
(45) Date of Patent: Sep. 30, 2025

(54) RAPIDLY INSERTABLE CENTRAL CATHETERS, INTRODUCERS, INSERTION DEVICES INCLUDING COMBINATIONS AND METHODS THEREOF

(71) Applicant: Bard Access Systems, Inc., Salt Lake City, UT (US)

(72) Inventors: Daniel B. Blanchard, Bountiful, UT (US); Glade H. Howell, Draper, UT (US); Joe Spataro, Cottonwood Heights, UT (US); Kyle G. Thornley, Farmington, UT (US); Austin J. Mckinnon, Herriman, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 680 days.

(21) Appl. No.: 17/750,097

(22) Filed: May 20, 2022

(65) Prior Publication Data

US 2022/0370762 A1 Nov. 24, 2022

Related U.S. Application Data

(60) Provisional application No. 63/284,533, filed on Nov. 30, 2021, provisional application No. 63/191,207, filed on May 20, 2021.

(51) Int. Cl.
*A61M 25/01* (2006.01)
*A61M 25/00* (2006.01)
*A61M 25/06* (2006.01)

(52) U.S. Cl.
CPC .... *A61M 25/0113* (2013.01); *A61M 25/0097* (2013.01); *A61M 25/0606* (2013.01); *A61M 25/0668* (2013.01); *A61M 2025/0675* (2013.01)

(58) Field of Classification Search
CPC ........ A61M 25/0113; A61M 25/09041; A61M 2025/0681; A61M 2025/0675; A61M 25/0668; A61M 2025/0183
See application file for complete search history.

(56) References Cited

U.S. PATENT DOCUMENTS 3,076,457 A 2/1963 Copen
3,359,978 A 12/1967 Smith, Jr.
(Continued)

FOREIGN PATENT DOCUMENTS

CN 106422031 B 7/2021
DE 4136051 A1 7/1993
(Continued)

OTHER PUBLICATIONS

PCT/US2022/021187 filed Mar. 21, 2022 International Search Report and Written Opinion dated Jun. 17, 2022.
(Continued)

*Primary Examiner* — Michael J Tsai
*Assistant Examiner* — Benjamin Koo
(74) *Attorney, Agent, or Firm* — Rutan & Tucker LLP

(57) ABSTRACT

Rapidly insertable central catheters ("RICCs"), introducers, and insertion devices including combinations and methods thereof are disclosed. For example, a RICC system can include an introducer and a RICC insertion assembly including a RICC assembly disposed in a RICC insertion device. The RICC assembly can include a RICC, an access guidewire, and a splittable casing over a catheter tube of the RICC and the access guidewire forming a longitudinal composite. The RICC insertion device can include a frame and a nose cover forming a split channel that splits away from a through channel of a nose of the frame. The RICC insertion device can be configured for advancing the RICC assembly by rolling the longitudinal composite across roller
(Continued)

Figure 1:
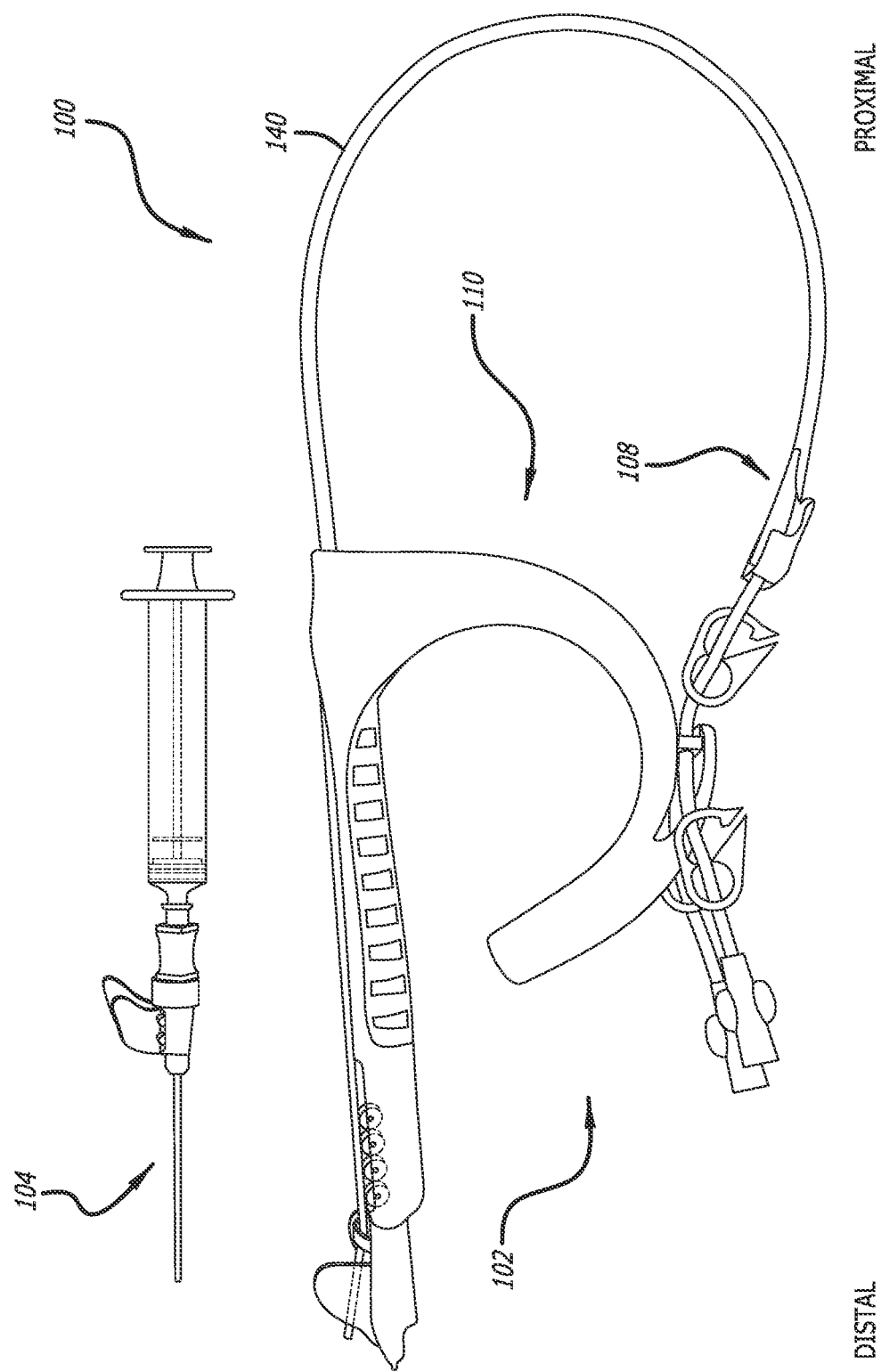

wheels disposed in the frame. The through channel can be configured for advancing the catheter tube therethrough while the split channel can be configured for both splitting and passing the splittable casing therethrough.

25 Claims, 27 Drawing Sheets

(56) References Cited

U.S. PATENT DOCUMENTS

| | | | |
|---|---|---|---|
| 4,743,265 | A | 5/1988 | Whitehouse et al. |
| 4,935,008 | A | 6/1990 | Lewis, Jr. |
| 4,994,040 | A | 2/1991 | Cameron et al. |
| 5,290,244 | A | 3/1994 | Moonka |
| 5,380,290 | A | 1/1995 | Makower et al. |
| 5,735,813 | A | 4/1998 | Lewis |
| 5,853,391 | A | 12/1998 | Bell |
| 5,971,957 | A | 10/1999 | Luther et al. |
| 6,019,736 | A | 2/2000 | Avellanet et al. |
| 6,159,195 | A | 12/2000 | Ha et al. |
| 8,882,713 | B1 | 11/2014 | Call et al. |
| 2002/0072712 | A1 | 6/2002 | Nool et al. |
| 2004/0092879 | A1 | 5/2004 | Kraus et al. |
| 2004/0236346 | A1 | 11/2004 | Parker |
| 2005/0021124 | A1 | 1/2005 | Cunniffe et al. |
| 2005/0043684 | A1 | 2/2005 | Basta et al. |
| 2007/0276288 | A1 | 11/2007 | Khaw |
| 2008/0027380 | A1 | 1/2008 | Wholey et al. |
| 2009/0187147 | A1 | 7/2009 | Kurth et al. |
| 2015/0224287 | A1 | 8/2015 | Bian et al. |
| 2015/0320968 | A1 | 11/2015 | Konstantino et al. |
| 2016/0175563 | A1 | 6/2016 | Woehr et al. |
| 2016/0220786 | A1* | 8/2016 | Mitchell ........... A61M 25/0029 |
| 2017/0035996 | A1 | 2/2017 | O'Fallon |
| 2017/0258489 | A1* | 9/2017 | Galili ..................... A61B 10/04 |
| 2017/0296792 | A1 | 10/2017 | Ornelas Vargas et al. |
| 2018/0043138 | A1 | 2/2018 | Chu |
| 2019/0015637 | A1 | 1/2019 | Jacobs |
| 2019/0038113 | A1 | 2/2019 | Chu |
| 2019/0134374 | A1 | 5/2019 | Korkuch et al. |
| 2020/0107859 | A1 | 4/2020 | Zhu |
| 2020/0147349 | A1 | 5/2020 | Holt |
| 2020/0170559 | A1 | 6/2020 | Burkholz et al. |
| 2020/0197682 | A1 | 6/2020 | Franklin et al. |
| 2021/0085927 | A1 | 3/2021 | Howell |
| 2021/0121661 | A1 | 4/2021 | Howell |
| 2021/0330941 | A1 | 10/2021 | Howell et al. |
| 2021/0361915 | A1 | 11/2021 | Howell et al. |
| 2021/0402153 | A1 | 12/2021 | Howell et al. |
| 2022/0362524 | A1 | 11/2022 | Howell |
| 2023/0039733 | A1 | 2/2023 | Howell |
| 2023/0041261 | A1 | 2/2023 | Howell |
| 2023/0043989 | A1 | 2/2023 | Howell |
| 2023/0064542 | A1 | 3/2023 | Howell |
| 2023/0086639 | A1 | 3/2023 | Howell |
| 2023/0149667 | A1 | 5/2023 | Lindekugel et al. |
| 2023/0201537 | A1 | 6/2023 | Howell et al. |
| 2023/0201538 | A1 | 6/2023 | Howell et al. |
| 2023/0218867 | A1 | 7/2023 | Howell et al. |
| 2023/0381481 | A1 | 11/2023 | Pizzato |
| 2024/0082549 | A1 | 3/2024 | Spataro et al. |
| 2024/0226507 | A1 | 7/2024 | Spataro |

FOREIGN PATENT DOCUMENTS

| | | |
|---|---|---|
| DE | 19750090 A1 | 6/1999 |
| EP | 0067260 A1 | 12/1982 |
| EP | 0155331 A1 | 9/1985 |
| EP | 0499147 A2 | 8/1992 |
| EP | 0641571 A1 | 3/1995 |
| EP | 3473291 A1 | 4/2019 |
| JP | H02255156 A | 10/1990 |
| JP | 2004254879 A | 9/2004 |
| JP | 2009232917 A | 10/2009 |
| WO | 8906986 A1 | 8/1989 |
| WO | 95/09662 A1 | 4/1995 |
| WO | 98/10821 A1 | 3/1998 |
| WO | 99/59651 A2 | 11/1999 |
| WO | 02/078776 A2 | 10/2002 |
| WO | 2005096778 A2 | 10/2005 |
| WO | 2009094089 A1 | 7/2009 |
| WO | 2011143621 A1 | 11/2011 |
| WO | 2012101089 A1 | 8/2012 |
| WO | 2013064215 A1 | 5/2013 |
| WO | 2015/061172 A1 | 4/2015 |
| WO | 2016042544 A1 | 3/2016 |
| WO | 2016123278 A1 | 8/2016 |
| WO | 2016187063 A1 | 11/2016 |
| WO | 2020206280 A2 | 10/2020 |
| WO | 2021216902 A1 | 10/2021 |
| WO | 2021222116 A2 | 11/2021 |
| WO | 2022/204049 A1 | 9/2022 |
| WO | 2022/246271 A2 | 11/2022 |
| WO | 2022/245774 A3 | 12/2022 |
| WO | 2023014994 A1 | 2/2023 |
| WO | 2023018669 A1 | 2/2023 |
| WO | 2023018729 A1 | 2/2023 |
| WO | 2023018733 A1 | 2/2023 |
| WO | 2023028138 A2 | 3/2023 |
| WO | 2023049174 A1 | 3/2023 |
| WO | 2023091586 A1 | 5/2023 |
| WO | 2023114324 A1 | 6/2023 |
| WO | 2023122312 A1 | 6/2023 |
| WO | 2023129457 A1 | 7/2023 |
| WO | 2023137077 A1 | 7/2023 |
| WO | 2024059073 A1 | 3/2024 |
| WO | 2024151869 A1 | 7/2024 |

OTHER PUBLICATIONS

PCT/US2022/030365 filed May 20, 2022 International Search Report and Written Opinion dated Apr. 4, 2023.
PCT/US2022/041368 filed Aug. 24, 2022 International Search Report and Written Opinion dated Mar. 21, 2023.
PCT/US2022/044242 filed Sep. 21, 2022 International Search Report and Written Opinion dated Feb. 8, 2023.
PCT/US2022/050280 filed Nov. 17, 2022 International Search Report and Written Opinion dated Apr. 17, 2023.
PCT/US2022/029561 filed May 17, 2022 International Search Report and Written Opinion dated Nov. 9, 2022.
PCT/US2022/039742 filed Aug. 8, 2022 International Search Report and Written Opinion dated Dec. 21, 2022.
PCT/US2022/039852 filed Aug. 9, 2022 International Search Report and Written Opinion dated Dec. 6, 2022.
PCT/US2022/039861 filed Aug. 9, 2022, International Search Report and Written Opinion dated Jan. 5, 2023.
PCT/US2023/032545 filed Sep. 12, 2023 International Search Report and Written Opinion dated Feb. 13, 2024.
U.S. Appl. No. 17/700,152, filed Mar. 21, 2022 Restriction Requirement dated Apr. 29, 2025.
U.S. Appl. No. 17/700,152, filed Mar. 21, 2022 Restriction Requirement dated Jan. 31, 2025.
U.S. Appl. No. 17/746,113, filed May 17, 2022 Non-Final Office Action dated Apr. 7, 2025.
U.S. Appl. No. 17/746,113, filed May 17, 2022 Restriction Requirement dated Dec. 11, 2024.
U.S. Appl. No. 17/884,307, filed Aug. 9, 2022 Non-Final Office Action dated Apr. 2, 2025.
PCT/US2022/039742 filed Aug. 8, 2022 International Preliminary Report on Patentability dated Feb. 13, 2024.
PCT/US2022/041368 filed Aug. 24, 2022 International Preliminary Report on Patentability dated Feb. 27, 2024.
PCT/US2022/044242 filed Sep. 21, 2022 International Preliminary Report on Patentability dated Mar. 26, 2024.
PCT/US2022/053887 filed Dec. 22, 2022 International Search Report and Written Opinion dated May 8, 2023.
PCT/US2022/052884 filed Dec. 14, 2022 International Search Report and Written Opinion dated May 15, 2023.

(56) References Cited

OTHER PUBLICATIONS

PCT/US2022/053724 filed Dec. 21, 2022 International Search Report and Written Opinion dated May 10, 2023.
PCT/US2023/010623 filed Jan. 11, 2023, International Search Report and Written Opinion dated Jul. 6, 2023.

* cited by examiner

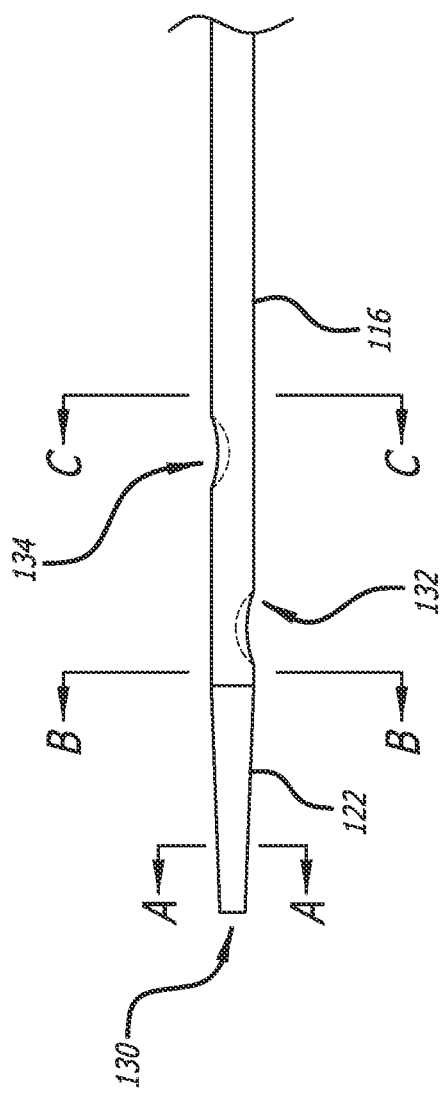
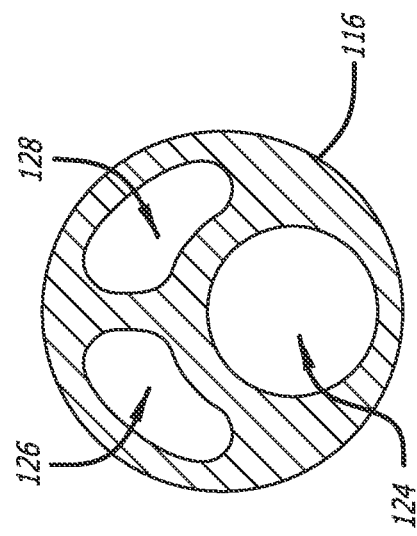
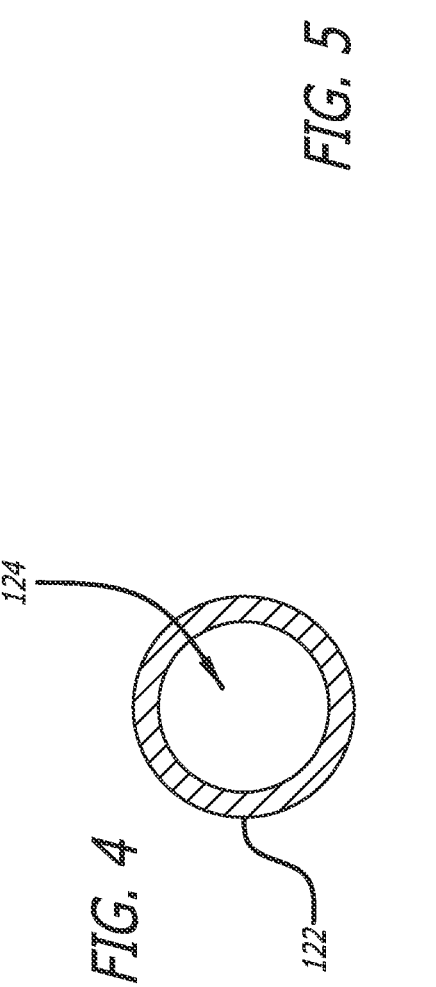
FIG. 3
FIG. 4
FIG. 5

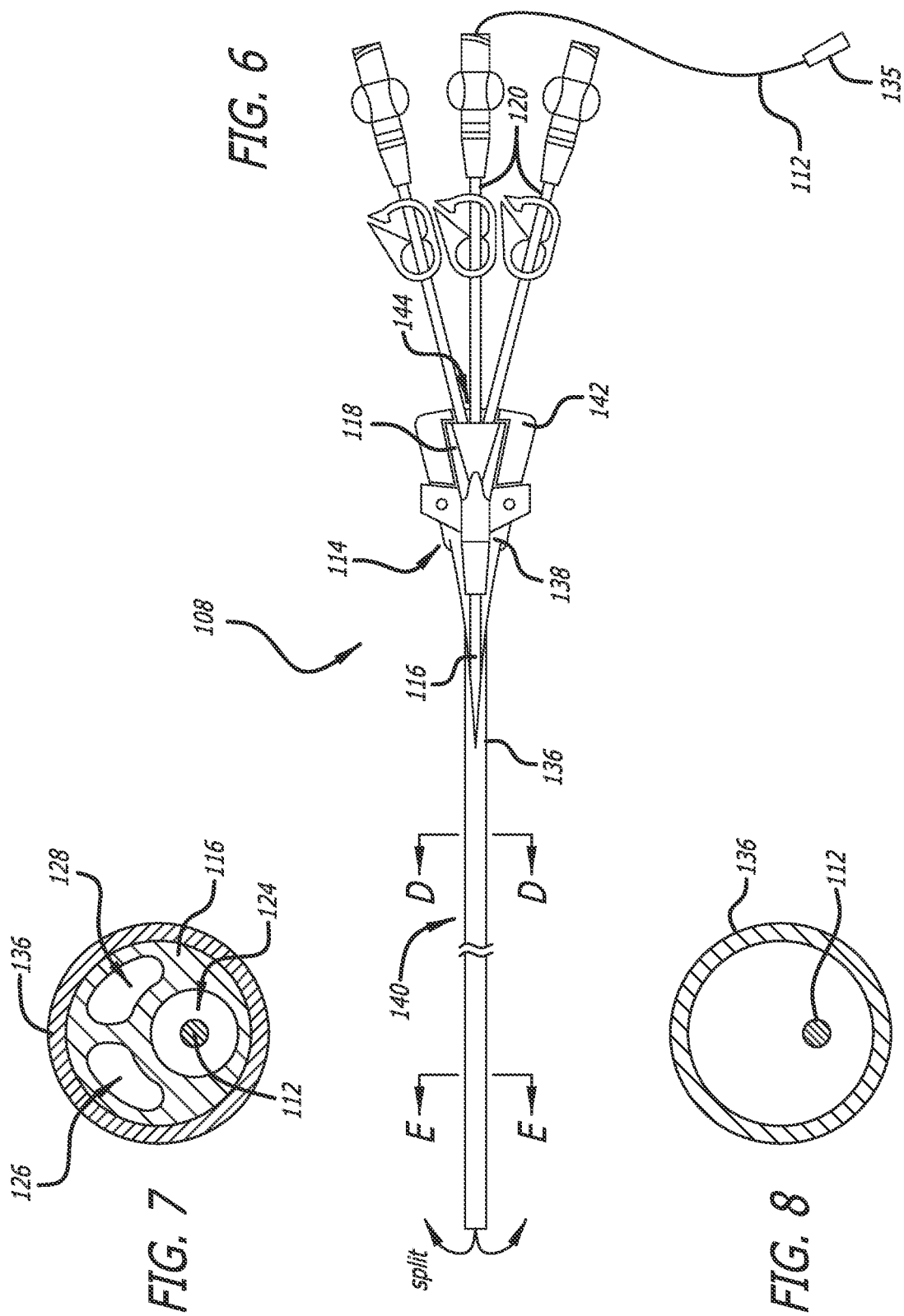

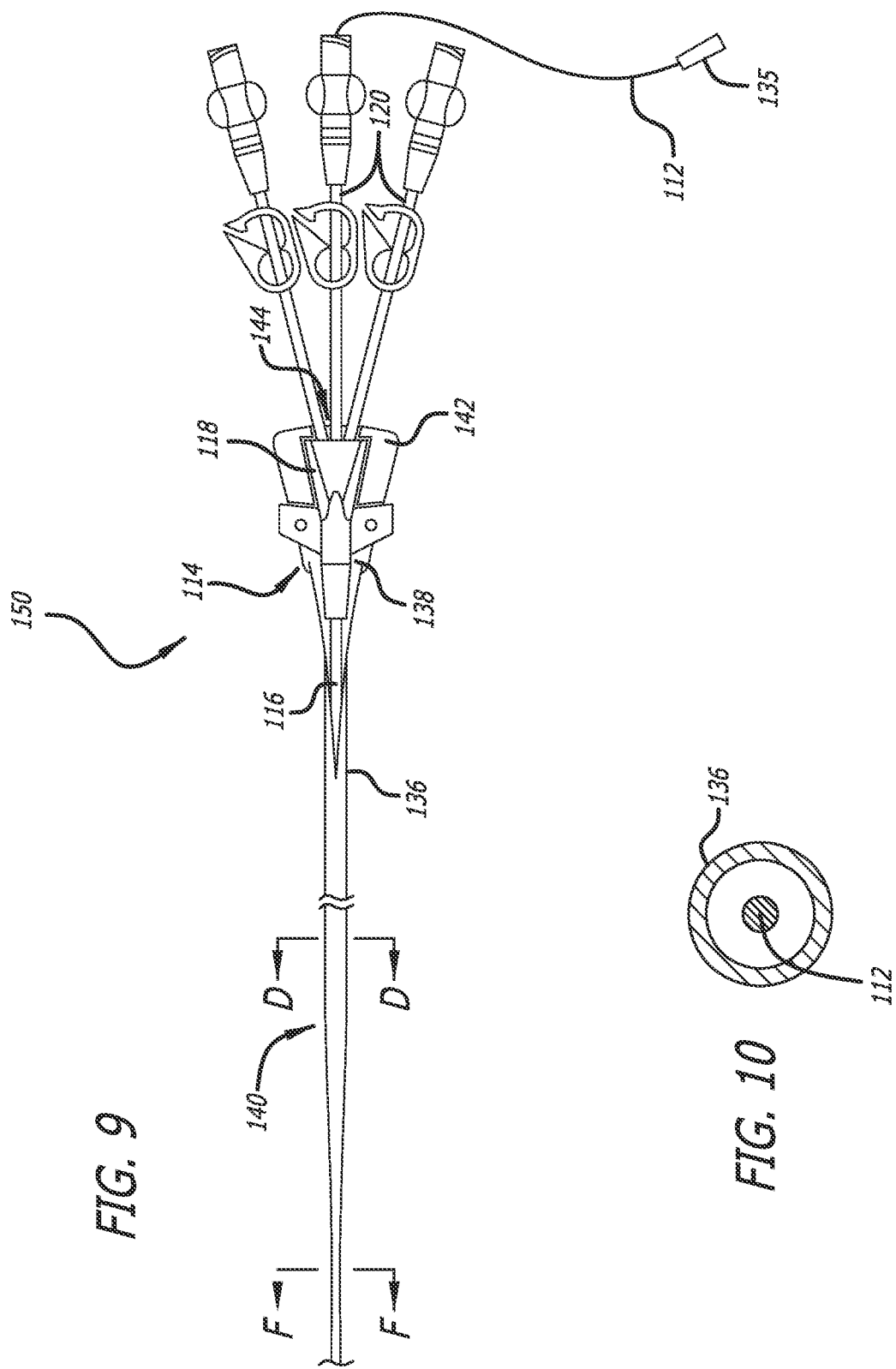

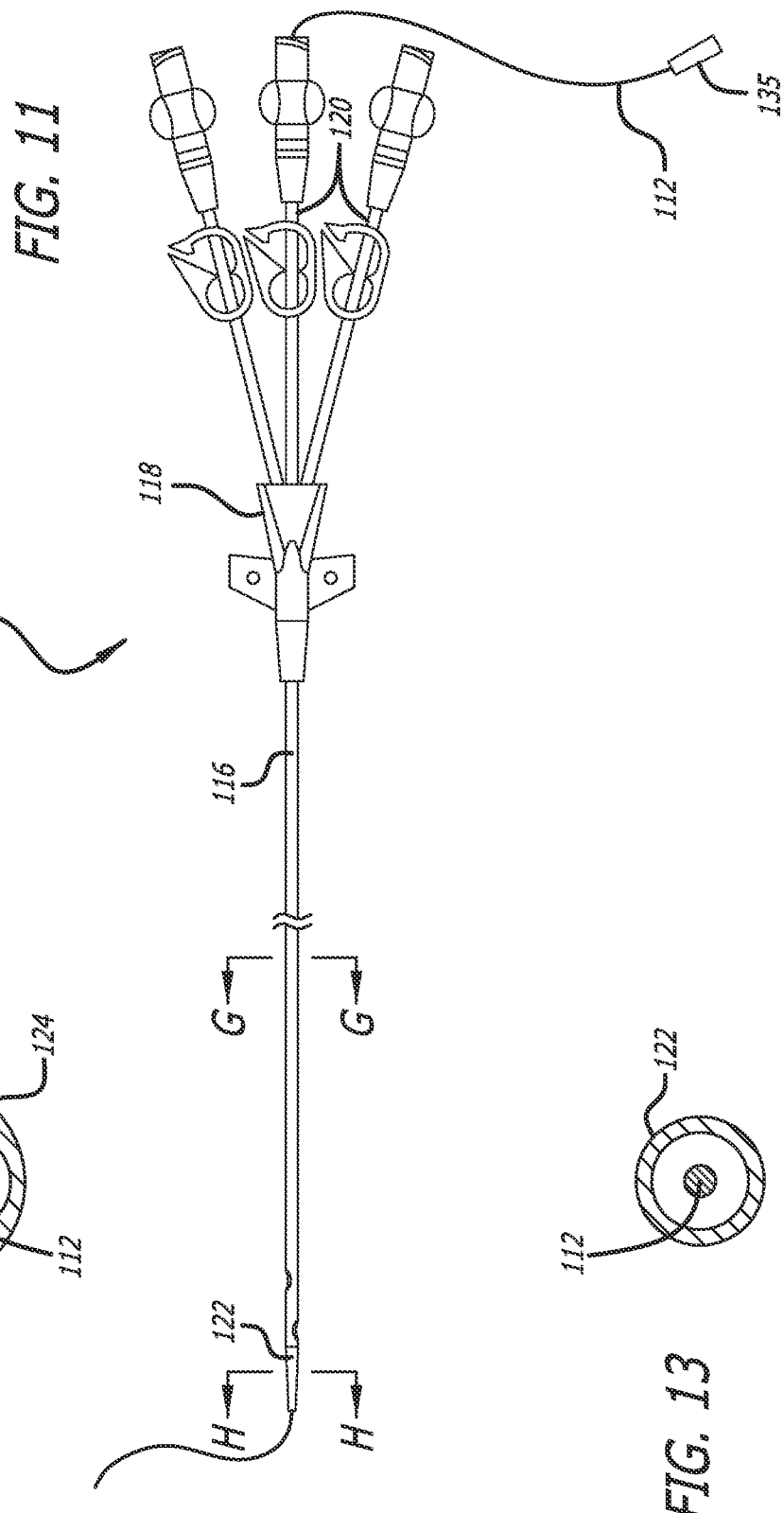
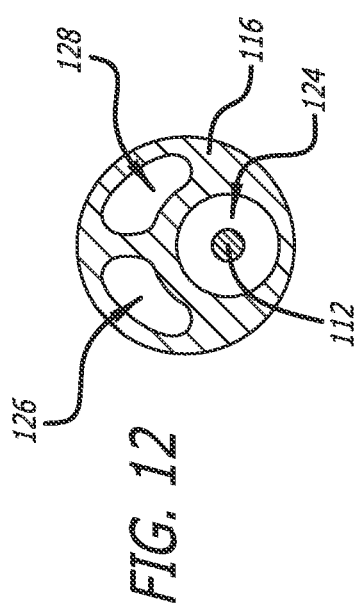
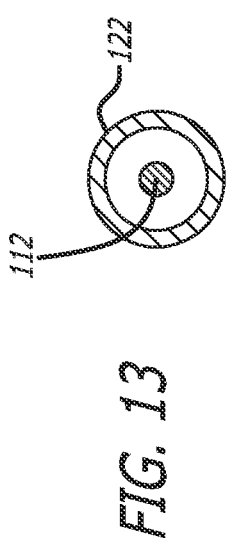
FIG. 11
FIG. 12
FIG. 13

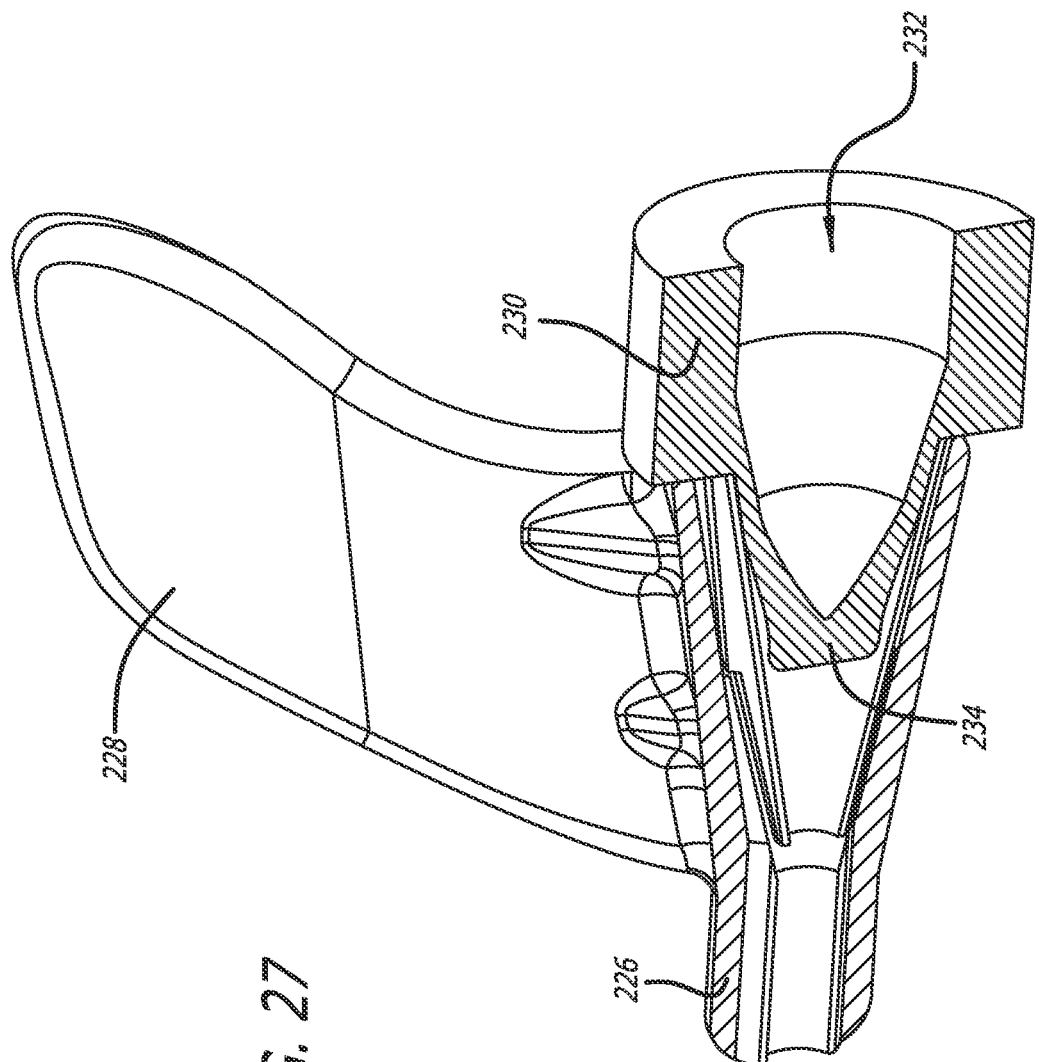

RAPIDLY INSERTABLE CENTRAL CATHETERS, INTRODUCERS, INSERTION DEVICES INCLUDING COMBINATIONS AND METHODS THEREOF

PRIORITY

This application claims the benefit of priority to U.S. Provisional Patent Application No. 63/191,207, filed May 20, 2021, and U.S. Provisional Patent Application No. 63/284,533, filed Nov. 30, 2021, each of which is incorporated by reference in its entirety into this application.

BACKGROUND

Central venous catheter ("CVCs") are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are rapidly insertable central catheters ("RICCs"), introducers, and insertion devices including combinations and methods thereof that address the foregoing.

SUMMARY

Disclosed herein is a RICC insertion system including a RICC assembly, a RICC insertion device, and an introducer. The RICC assembly includes a RICC, an access guidewire, and a keeper. The RICC includes a catheter tube, a catheter hub coupled to a proximal portion of the catheter tube, and one or more extension legs. Each extension leg of the one-or-more extension legs is coupled to the catheter hub by a distal portion thereof. The access guidewire is disposed in a primary lumen of the RICC. The keeper includes a splittable casing over both the catheter tube and a distal portion of the access guidewire extending from a distal end of the RICC forming a longitudinal composite thereof. The RICC insertion device includes a frame, one or more roller wheels, and a nose cover over a nose of the frame. The frame includes a longitudinal handle, the nose, and a curved cradle. The handle includes a wheel well. The nose extends from a distal portion of the handle distal of the wheel well. The nose includes a through channel configured for advancing the catheter tube of the RICC therethrough. The cradle extends from a proximal portion of the handle. The one-or-more roller wheels are disposed in the wheel well. The nose cover and nose form a split channel configured for both splitting and passing the splittable casing therethrough. The RICC insertion device is configured for advancing the RICC assembly from an initial position in the frame to a final position in the frame. This is accomplished by repeatedly pushing the longitudinal composite into the one-or-more roller wheels and rolling the longitudinal composite across the one-or-more roller wheels.

In some embodiments, the keeper further includes a catheter-hub holder to which a proximal end of the splittable casing is attached. The catheter-hub holder is configured to hold the catheter hub therein as well as keep the splittable casing in position over the catheter tube and the access guidewire.

In some embodiments, the catheter-hub holder includes a perimetrical wall around at least a portion of a perimeter of the catheter-hub holder. The perimetrical wall defines a recess into which the catheter hub fits with an engineering fit.

In some embodiments, the cradle includes a curved extension over a distal portion of the cradle. The extension substantially follows a same curve as the cradle.

In some embodiments, the cradle includes an enclosure over the distal portion of the cradle with the extension extending therefrom. The enclosure is configured to enclose therein an otherwise exposed proximal portion of the access guidewire in the initial position of the RICC assembly in the frame.

In some embodiments, the RICC insertion device further includes a retaining clip. The retaining clip is configured to clip on to a proximal portion of the RICC and retain the RICC assembly in the RICC insertion device. The retaining clip is also configured to keep the catheter tube from prematurely advancing over the access guidewire. The retaining clip includes a post configured to engage with a slot in the extension that faces an open face of the cradle.

In some embodiments, the retaining clip is configured to disengage with the slot in the extension when any remaining slack of the longitudinal composite is removed upon advancing the RICC assembly from the initial position to the final position in the frame.

In some embodiments, the frame further includes a retaining arch over the cradle proximate the proximal portion of the handle from which the cradle extends. The retaining arch is configured to retain the RICC assembly in the RICC insertion device. The retaining arch is also configured to hold the longitudinal composite over the handle as the RICC assembly transitions over the proximal portion of the handle from which the cradle extends upon advancing the RICC assembly from the initial position to the final position in the frame.

In some embodiments, the nose cover and the nose further form a retaining clamp configured to slidably clamp the longitudinal composite therein. The nose cover is rotatable over the nose. The nose cover includes a longitudinal gap configured to rotatably align with the through channel in the nose for removal of the longitudinal composite, the splittable casing, or the catheter tube therefrom.

In some embodiments, the RICC insertion device further includes a retractable nicking blade. The retractable nicking blade is disposed in a nicking-blade carriage slidably integrated into the nose. The nicking-blade carriage has a nicking position with the retractable nicking blade extending beyond a distal end of the nose. The nicking-blade carriage also has a safety position with the retractable nicking blade short of the distal end of the nose.

In some embodiments, the introducer includes an introducer needle and a splittable introducer sheath. The introducer needle includes a needle shaft and a needle hub. The needle shaft includes a needle tip in a distal portion of the needle shaft. The needle hub is coupled to a proximal portion of the needle shaft. The introducer sheath is configured to accept therein the introducer needle. The introducer sheath includes a splittable sheath body and a splittable sheath hub coupled to a proximal portion of the sheath body. The sheath hub includes a pair of outwardly extending wings along a length of the sheath hub. The wings have an internal angle of about 90° or less between the wings. The wings are configured for splitting the sheath hub by pinching the wings together with a single hand.

In some embodiments, the sheath hub includes a single longitudinal fault along a side of the sheath hub opposite a vertex of the internal angle formed by the wings. The sheath hub is configured to split along the fault for propagation along a same side of the sheath body when the wings are pinched together.

In some embodiments, the sheath hub includes a pair of longitudinal faults including a primary fault and a secondary fault. The primary fault extends along a primary side of the sheath hub opposite a vertex of the internal angle formed by the wings. The secondary fault extends along a secondary side of the sheath hub opposite the primary fault. The sheath hub is configured to split along the primary fault for propagation along the primary side of the sheath body when the wings are pinched together. The sheath hub is also configured to split along the secondary fault for propagation along the secondary side of the sheath body when the wings are pulled apart.

In some embodiments, the sheath hub further includes a valved cap disposed in a proximal portion of the sheath hub. The valved cap includes a tapered female valved-cap connector and a septum distal of a proximal opening in the female valved-cap connector. The female valved-cap connector is configured to accept therein a tapered male needle-hub connector extending from a distal portion of the needle hub. The septum is configured to accept therethrough the needle shaft.

In some embodiments, the valved cap is partially or fully split such that the valved cap splits with the sheath hub when the wings are pinched together.

In some embodiments, the sheath hub further includes an overmolded nicking blade and a hinged nicking-blade cover. The overmolded nicking blade distally extends from the sheath hub. The nicking-blade cover has an opened state with the nicking-blade cover opened away from the overmolded nicking blade. The nicking-blade cover also has a closed state with the nicking-blade cover closed over the overmolded nicking blade.

In some embodiments, the introducer further includes a syringe. The syringe includes a tapered male syringe tip extending from a distal portion of the syringe. The syringe tip is configured to insert into a tapered female needle-hub connector in a proximal portion of the needle hub.

Also disclosed herein is a RICC insertion assembly including, in some embodiments, a RICC assembly and a RICC insertion device. The RICC assembly includes a RICC, an access guidewire, and a keeper. The RICC includes a catheter tube, a catheter hub coupled to a proximal portion of the catheter tube, and one or more extension legs. Each extension leg of the one-or-more extension legs is coupled to the catheter hub by a distal portion thereof. The access guidewire is disposed in a primary lumen of the RICC. The keeper includes a splittable casing over both the catheter tube and a distal portion of the access guidewire extending from a distal end of the RICC forming a longitudinal composite thereof. The RICC insertion device includes a frame, one or more roller wheels, and a nose cover over a nose of the frame. The frame includes a longitudinal handle, the nose, and a curved cradle. The handle includes a wheel well. The nose extends from a distal portion of the handle distal of the wheel well. The nose includes a through channel configured for advancing the catheter tube of the RICC therethrough. The cradle extends from a proximal portion of the handle. The one-or-more roller wheels are disposed in the wheel well. The nose cover and nose form a split channel configured for both splitting and passing the splittable casing therethrough. The RICC insertion device is configured for advancing the RICC assembly from an initial position in the frame to a final position in the frame. This is accomplished by repeatedly pushing the longitudinal composite into the one-or-more roller wheels and rolling the longitudinal composite across the one-or-more roller wheels.

In some embodiments, a distal end of the longitudinal composite, the splittable casing, or the access guidewire is substantially commensurate with a distal end of the frame in the initial position of the RICC assembly in the frame.

In some embodiments, a slack loop of the longitudinal composite extends away from both the handle and the cradle in the initial position of the RICC assembly in the frame.

In some embodiments, the longitudinal composite is substantially split in the final position of the RICC assembly in the frame.

In some embodiments, a proximal end of an extension leg or a Luer connector coupled to the extension leg of the one-or-more extension legs of the RICC is substantially commensurate with a proximal end of the cradle in the initial position of the RICC assembly in the frame.

In some embodiments, a proximal end of the access guidewire is coupled to the proximal end of the cradle in the initial position of the RICC assembly in the frame.

In some embodiments, the one-or-more extension legs of the RICC lie substantially over the handle in the final position of the RICC assembly in the frame.

In some embodiments, the catheter hub of the RICC lies over the wheel well in the final position of the RICC assembly in the frame.

Also disclosed herein is a method for inserting a RICC into a blood-vessel lumen of a patient. The method includes, in some embodiments, an obtaining step, a needle tract-establishing step, an introducer needle-removing step, an access guidewire-advancing step, an introducer sheath-removing step, and a catheter tube-advancing step. The obtaining step includes obtaining a RICC insertion system. The RICC insertion system includes an introducer, a RICC insertion device, and a RICC assembly including the RICC. The RICC assembly is optionally already disposed in the RICC insertion device in a substantially ready-to-operate state of a RICC insertion assembly. The needle tract-establishing step includes establishing a needle tract from an area of skin into the blood-vessel lumen of the patient with an introducer needle of the introducer. The introducer needle is disposed in a splittable introducer sheath of the introducer for the establishing of the needle tract. The introducer needle-removing step includes removing the introducer needle from the introducer sheath leaving the introducer sheath in the blood-vessel lumen. The access guidewire-advancing step includes advancing an access guidewire through a nose and nose cover of the RICC insertion device, through a splittable sheath hub of the introducer, through the introducer sheath, and into the blood-vessel lumen. The access guidewire-advancing step is accomplished, in part, by splitting a splittable casing away from a longitudinal composite of the RICC assembly. A distal portion of the access guidewire that extends from a primary-lumen aperture of a catheter tube of the RICC is freed from the longitudinal composite with the splitting of the splittable casing for the advancing of the access guidewire. The introducer sheath-removing step includes removing the introducer sheath leaving the access guidewire in the blood-vessel lumen. The catheter tube-advancing step includes advancing the catheter tube over the access guidewire and into the blood-vessel lumen. The catheter tube-advancing step is accomplished, in part, by further splitting the splittable casing away from the longitudinal composite of the RICC assembly. The catheter tube is freed from the longitudinal composite with the splitting of the splittable casing, which allows the catheter tube to be advanced over the access guidewire upon removal of any remaining slack of the longitudinal composite in the RICC insertion assembly.

In some embodiments, needle tract-establishing step includes ensuring blood flashes back into a needle hub of the introducer needle for confirmation the needle tract extends into the blood-vessel lumen.

In some embodiments, the method further includes a blood-aspirating step. The blood-aspirating step includes aspirating blood with a syringe coupled to the introducer needle for confirmation the needle tract extends into the blood-vessel lumen. The blood-aspirating step is performed before the introducer needle-removing step.

In some embodiments, the method further includes an introducer sheath-advancing step. The introducer sheath-advancing step includes advancing the introducer sheath over the introducer needle and farther into the blood-vessel lumen. The introducer sheath-advancing step is performed before the introducer needle-removing step.

In some embodiments, the method further includes a connector-connecting step. The connector-connecting step includes inserting a male nose connector of the nose of the RICC insertion device into a female valved-cap connector of the sheath hub of the introducer sheath. The connector-connecting step is performed before the access guidewire-advancing step.

In some embodiments, the method further includes a skin-nicking step. The skin-nicking step includes nicking the area of skin around the needle tract with a nicking blade extending from the sheath hub. The skin-nicking step is performed when the catheter tube is 7 Fr or larger. The skin-nicking step is also performed before the access guidewire-advancing step.

In some embodiments, the method further includes a cover-opening step and a cover-closing step. The cover-opening step includes opening a hinged nicking-blade cover away from the nicking blade and into a nicking position away from the nicking blade. The cover-opening step is performed before the skin-nicking step. The cover-closing step includes closing the nicking-blade cover over the nicking blade into a safety position over the nicking blade. The cover-closing step is performed after the skin-nicking step.

In some embodiments, the method further includes an alternative skin-nicking step. The alternative skin-nicking step includes nicking the area of skin around the needle tract with a retractable nicking blade integrated into the nose of the RICC insertion device. The alternative skin-nicking step is performed when the catheter tube is 7 Fr or larger. The alternative skin-nicking step is also performed before the catheter tube-advancing step.

In some embodiments, the method further includes a pair of carriage-sliding steps including a first carriage-sliding step and a second carriage-sliding step. The first carriage-sliding step includes distally sliding a nicking-blade carriage including the nicking blade overmolded therein into a nicking position such that the nicking blade extends beyond a distal end of the nose of the RICC insertion device. The second carriage-sliding step includes proximally sliding the nicking-blade carriage into a safety position such that the nicking blade is short of the distal end of the nose of the RICC insertion device.

In some embodiments, the introducer sheath-removing step includes splitting the introducer sheath to form a split along a side of the introducer sheath by pinching together a pair of wings outwardly extending from the sheath hub. The introducer sheath-removing step also includes propagating the split in a side of the sheath hub along a same side of a sheath body of the introducer.

In some embodiments, the access guidewire-advancing step or the catheter tube-advancing step includes repeatedly pushing the longitudinal composite into one or more roller wheels disposed in a wheel well of a longitudinal handle of the RICC insertion device and rolling the longitudinal composite across the one-or-more roller wheels with a single hand to split the splittable casing away from the longitudinal composite.

In some embodiments, the access guidewire-advancing step or the catheter tube-advancing step includes pulling the splittable casing of the longitudinal composite out of a split channel formed between the nose of the RICC insertion device and the nose cover thereover to split the splittable casing away from the longitudinal composite.

In some embodiments, a retaining clip clipped on to a proximal portion of the RICC disengages with a curved extension over a cradle of the RICC insertion device upon removal of any remaining slack of the longitudinal composite in the RICC insertion assembly, thereby allowing the catheter tube to advance over the access guidewire.

In some embodiments, the method further includes an access guidewire-removing step. The access guidewire-removing step includes removing the access guidewire leaving the catheter tube in the blood-vessel lumen.

In some embodiments, the method further includes a keeper-removing step. The keeper-removing step includes removing a keeper including a proximal end of the splittable casing attached to a catheter-hub holder from the RICC assembly. The keeper-removing step is accomplished, in part, by removing a catheter hub of the RICC from the catheter-hub holder and splitting any remaining splittable casing of the longitudinal composite away from the catheter tube.

In some embodiments, the method further includes a catheter tube-freeing step. The catheter tube-freeing step includes freeing the catheter tube of the RICC from a retaining clamp formed of the nose and nose cover of the RICC insertion device. The catheter tube-freeing step is accomplished, in part, by rotating the nose cover over the nose to align a longitudinal gap of the nose cover with a through channel in the nose and pulling the catheter tube away from the RICC insertion device.

Also disclosed herein is a catheter insertion system for a RICC assembly including, in some embodiments, an insertion assembly having a housing including a blood-flash nozzle and a catheter nozzle; a blood-flash indicator in fluid communication with the blood-flash nozzle; a RICC disposed within an interior cavity of the housing and slidably engaged with the catheter nozzle; and an introducer including an introducer needle and an introducer sheath, the introducer releasably engaged with one of the blood-flash nozzle or a catheter nozzle.

In some embodiments, the catheter insertion system further includes a needle-retraction system coupled with the introducer needle. The needle-retraction system is configured to withdraw the introducer needle from the introducer sheath proximally through the blood-flash nozzle.

In some embodiments, the blood-flash indicator is in fluid communication with a needle lumen of the needle.

In some embodiments, a sheath hub of the introducer sheath is configured to releasably engage the catheter nozzle and longitudinally align a sheath lumen of the sheath with the RICC.

In some embodiments, the catheter insertion system further includes a catheter-advancement assembly configured to slidably engage with the RICC with the catheter nozzle.

In some embodiments, the catheter insertion system further includes an access guidewire coupled to a guidewire-advancement assembly. The guidewire-advancement assembly is configured to slidably engage the access guidewire with the catheter nozzle.

Also disclosed herein is a method of placing a catheter within a vasculature of a patient including, in some embodiments, accessing a vasculature with an introducer needle of an introducer; withdrawing the introducer needle from a sheath lumen of an introducer sheath of the introducer through a blood-flash nozzle of an insertion assembly; detaching a sheath hub of the introducer sheath from the blood-flash nozzle and engaging the sheath hub with a catheter nozzle of the insertion assembly; advancing an access guidewire through the catheter nozzle and the sheath lumen; splitting the introducer sheath longitudinally to disengage the introducer sheath from the access guidewire; and advancing the catheter through the catheter nozzle over the access guidewire.

In some embodiments, the method further includes actuating a blood-flash indicator to draw a fluid flow proximally through a needle lumen of the introducer needle and through the blood-flash nozzle.

In some embodiments, the method further includes actuating a needle-retraction assembly, disposed within the insertion assembly, to withdraw the introducer needle through the blood-flash nozzle and into an interior cavity of the insertion assembly.

In some embodiments, the catheter includes one of a rapidly insertable central catheter, a central venous catheter, a peripherally inserted central catheter, or a dialysis catheter.

These and other features of the concepts provided herein will become more apparent to those of skill in the art in view of the accompanying drawings and following description, which describe particular embodiments of such concepts in greater detail.

DRAWINGS

FIG. 1 provides a RICC insertion system including a RICC insertion assembly and an introducer in accordance with some embodiments.

Figure 2:
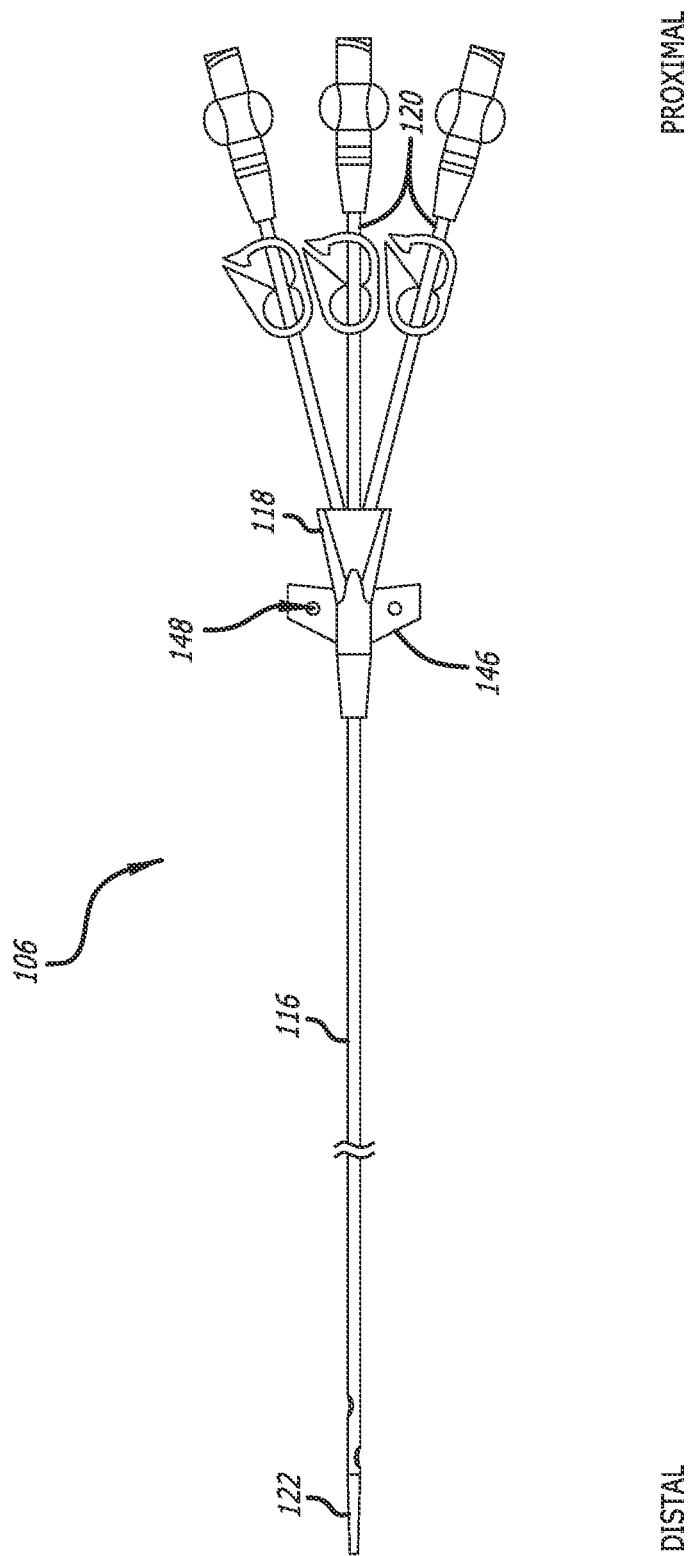

FIG. 2 provides a RICC in accordance with some embodiments.

FIG. 3 provides a distal portion of the RICC in accordance with some embodiments.

FIG. 4 provides a first transverse cross section of the RICC in accordance with some embodiments.

FIG. 5 provides a second or third transverse cross section of the RICC in accordance with some embodiments.

FIG. 6 provides a RICC assembly in accordance with some embodiments.

FIG. 7 provides a first transverse cross section of the RICC assembly in accordance with some embodiments.

FIG. 8 provides a second transverse cross section of the RICC assembly in accordance with some embodiments.

FIG. 9 provides a first alternative RICC assembly in accordance with some embodiments.

FIG. 10 provides a transverse cross section of the first alternative RICC assembly in accordance with some embodiments.

FIG. 11 provides a second alternative RICC assembly in accordance with some embodiments.

FIG. 12 provides a first transverse cross section of the second alternative RICC assembly in accordance with some embodiments.

FIG. 13 provides a second transverse cross section of the second alternative RICC assembly in accordance with some embodiments.

Figure 14:
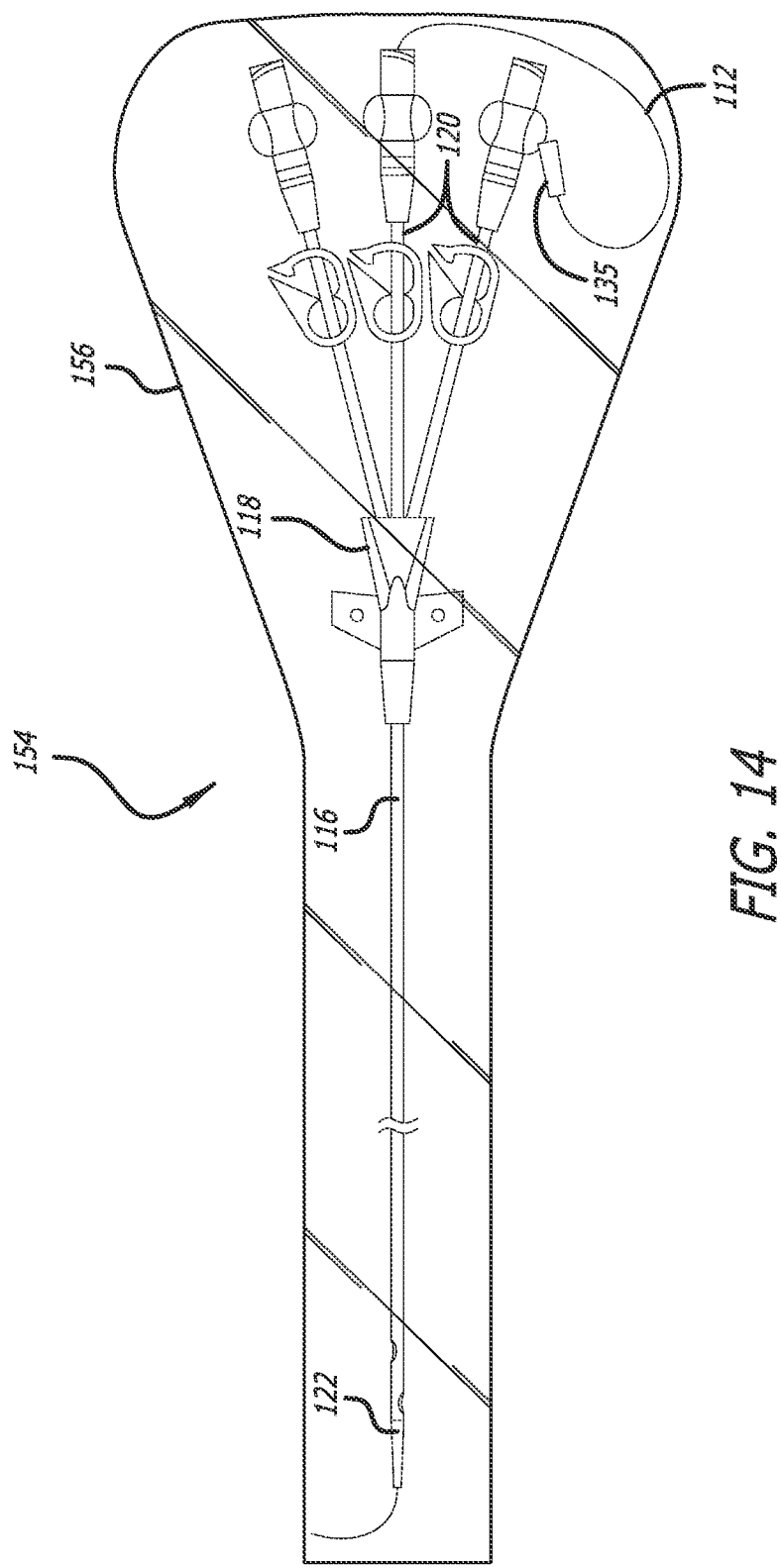

FIG. 14 provides a third alternative RICC assembly in accordance with some embodiments.

Figure 15A:
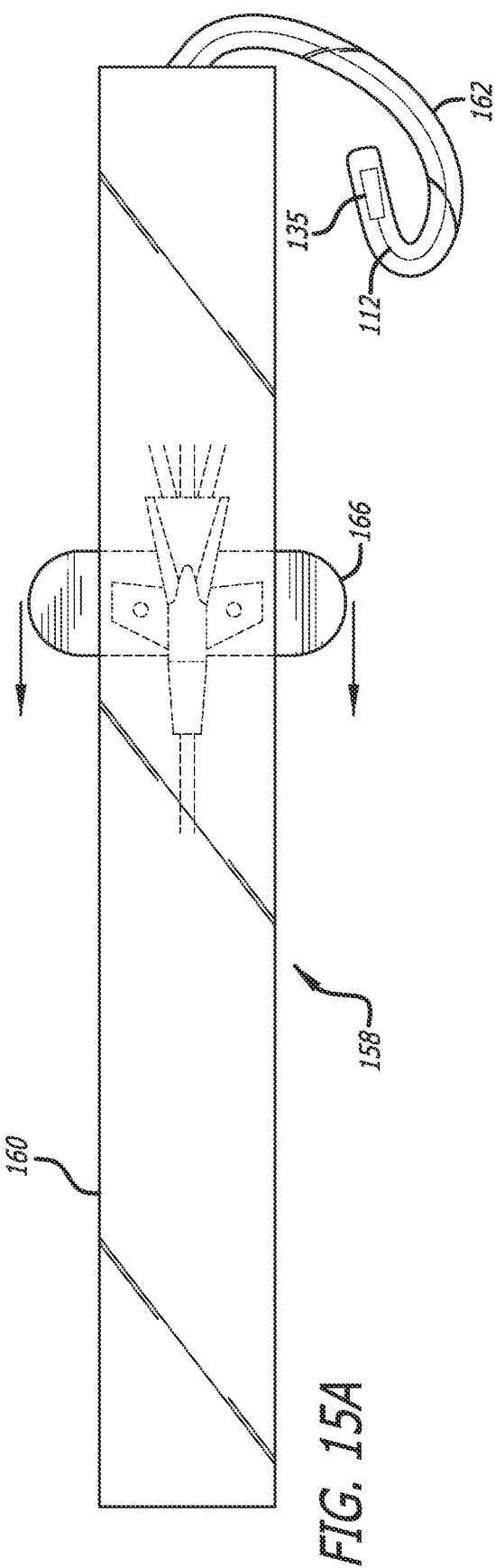

FIG. 15A provides a top view of a fourth alternative RICC assembly in accordance with some embodiments.

Figure 15B:
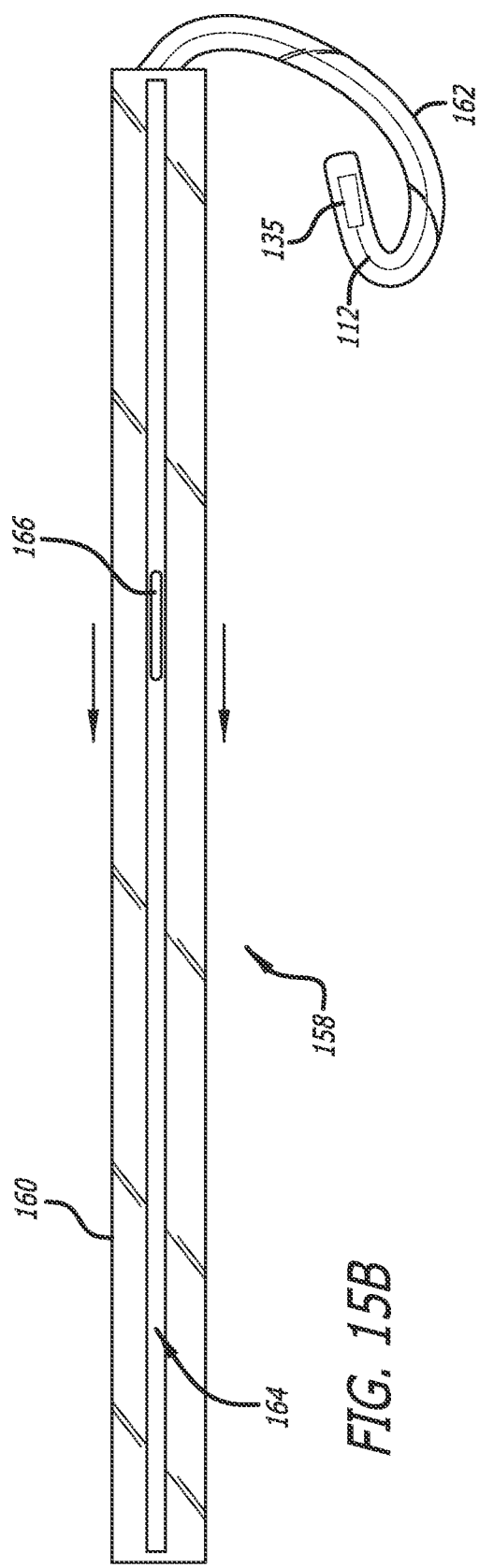

FIG. 15B provides a side view of the fourth alternative RICC assembly in accordance with some embodiments.

Figure 16:
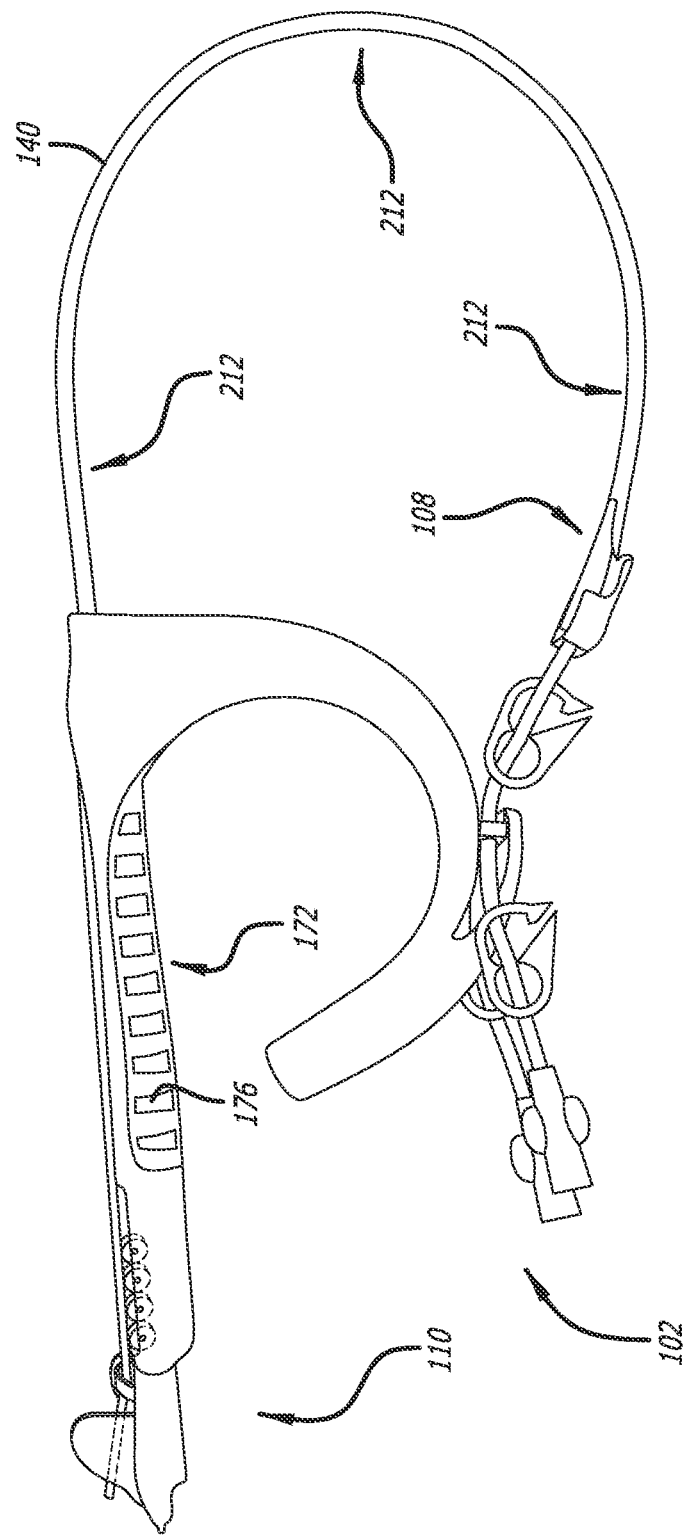

FIG. 16 provides a RICC insertion assembly including the RICC assembly disposed in a RICC insertion device in a ready-to-operate state of the RICC insertion assembly in accordance with some embodiments.

Figure 17:
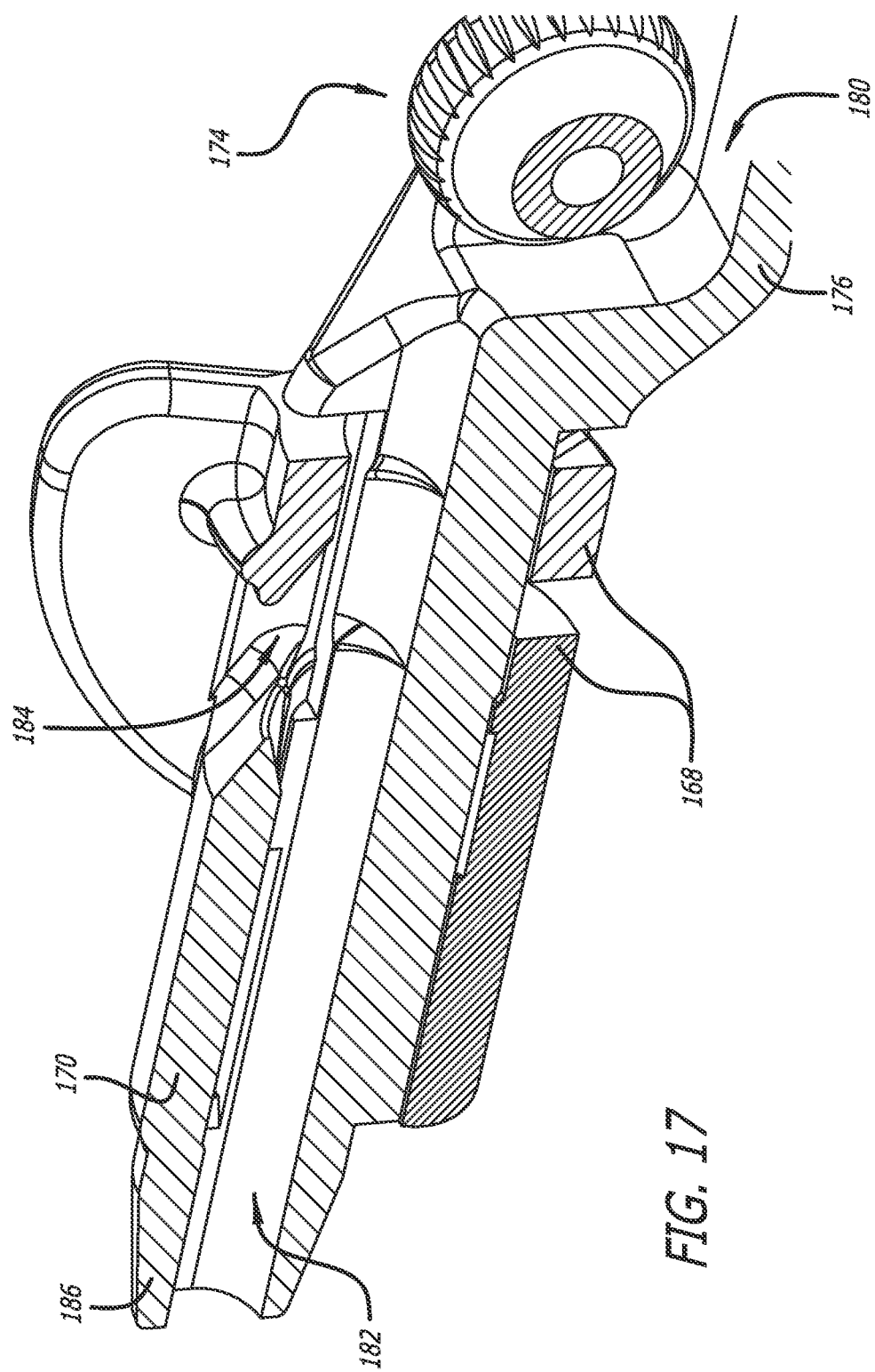

FIG. 17 provides a nose cover over a nose of the RICC insertion device in accordance with some embodiments.

Figure 18B:
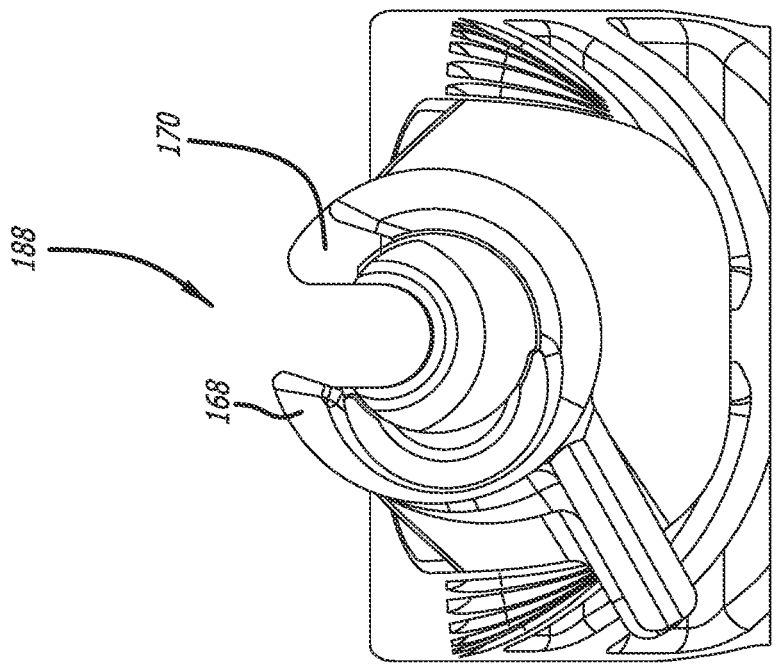
Figure 18A:
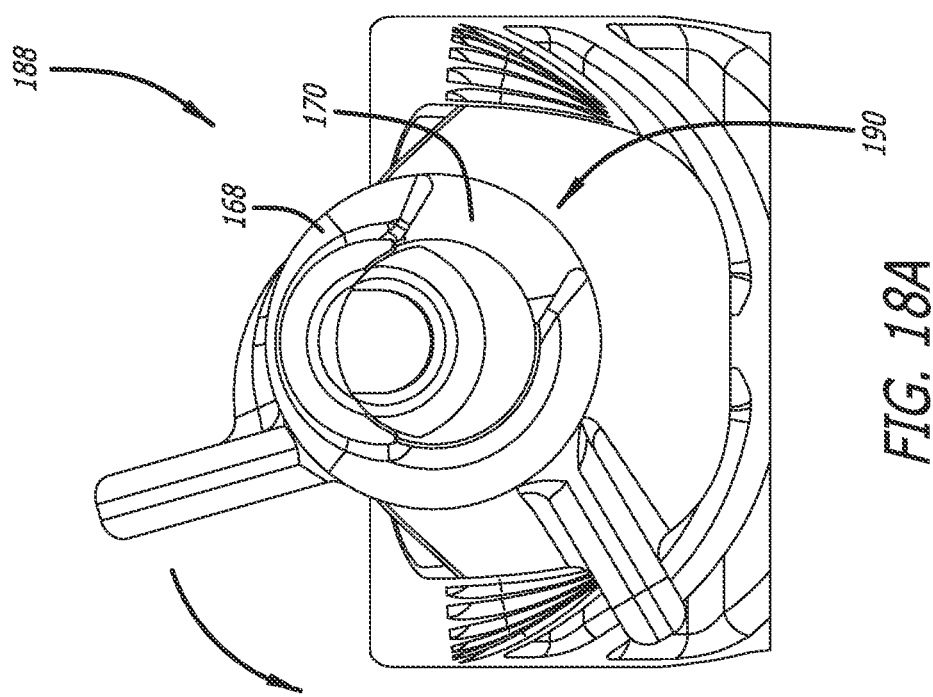

FIG. 18A provides a retaining clamp formed between the nose cover and the nose of the RICC insertion device when the retaining clamp is in a closed state in accordance with some embodiments.

FIG. 18B provides the retaining clamp when the retaining clamp is in an open state in accordance with some embodiments.

Figure 19:
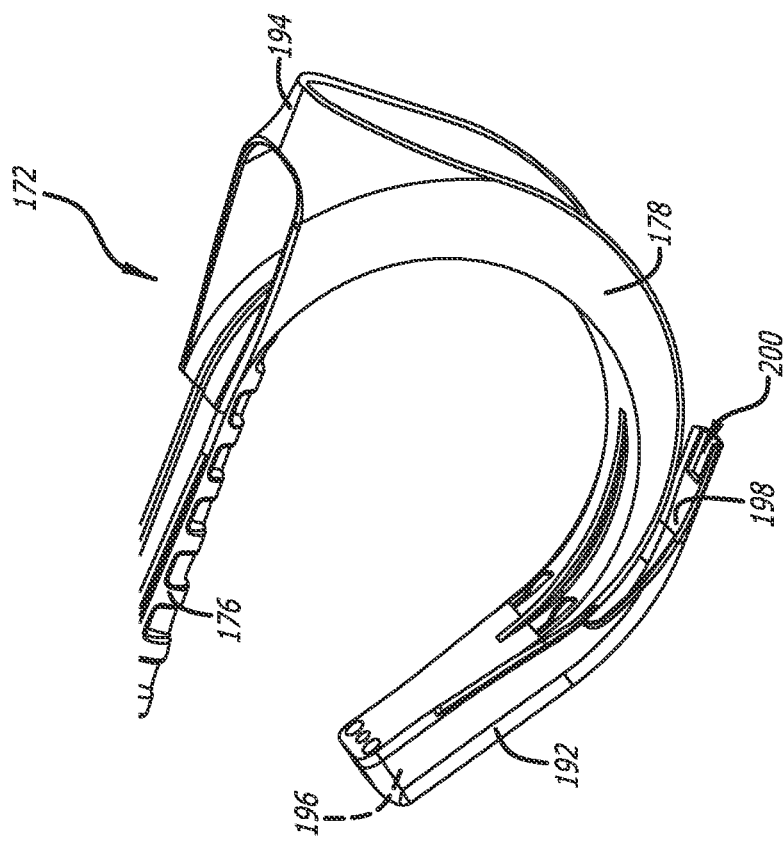

FIG. 19 provides a curved extension of a curved cradle of the RICC insertion device including a slot configured to engage with the retaining clip in accordance with some embodiments.

Figure 20:
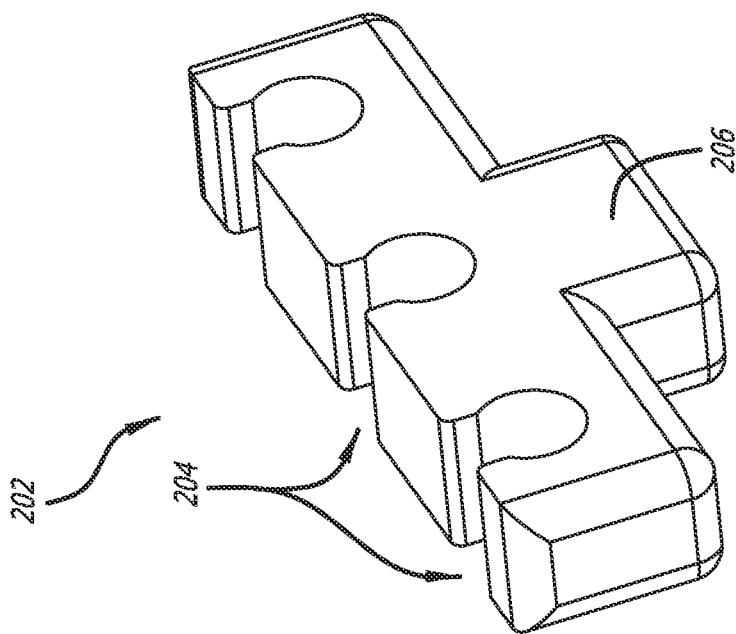

FIG. 20 provides a retaining clip of the RICC insertion device in accordance with some embodiments.

Figure 21B:
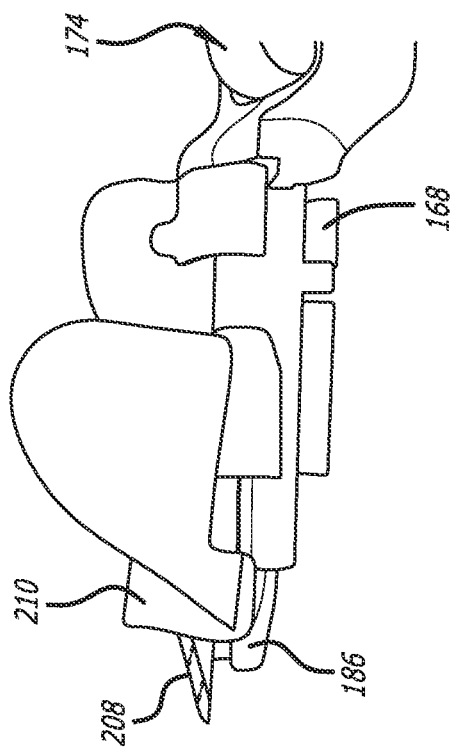
Figure 21A:
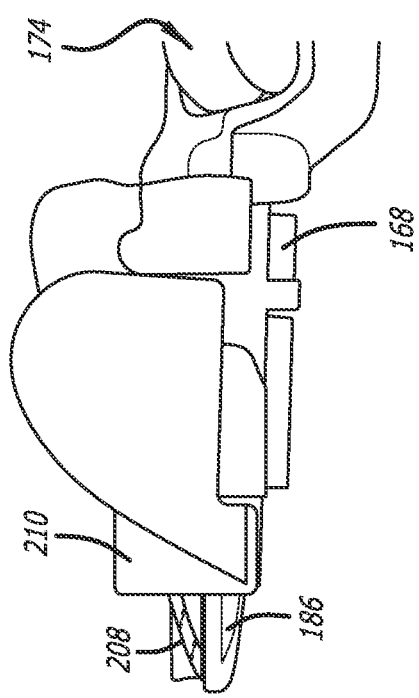

FIG. 21A provides a retractable nicking blade integrated into the nose of the RICC insertion device when the nicking blade is in a safety position in accordance with some embodiments.

FIG. 21B provides the retractable nicking blade when the nicking blade is in a nicking position in accordance with some embodiments.

Figure 22:
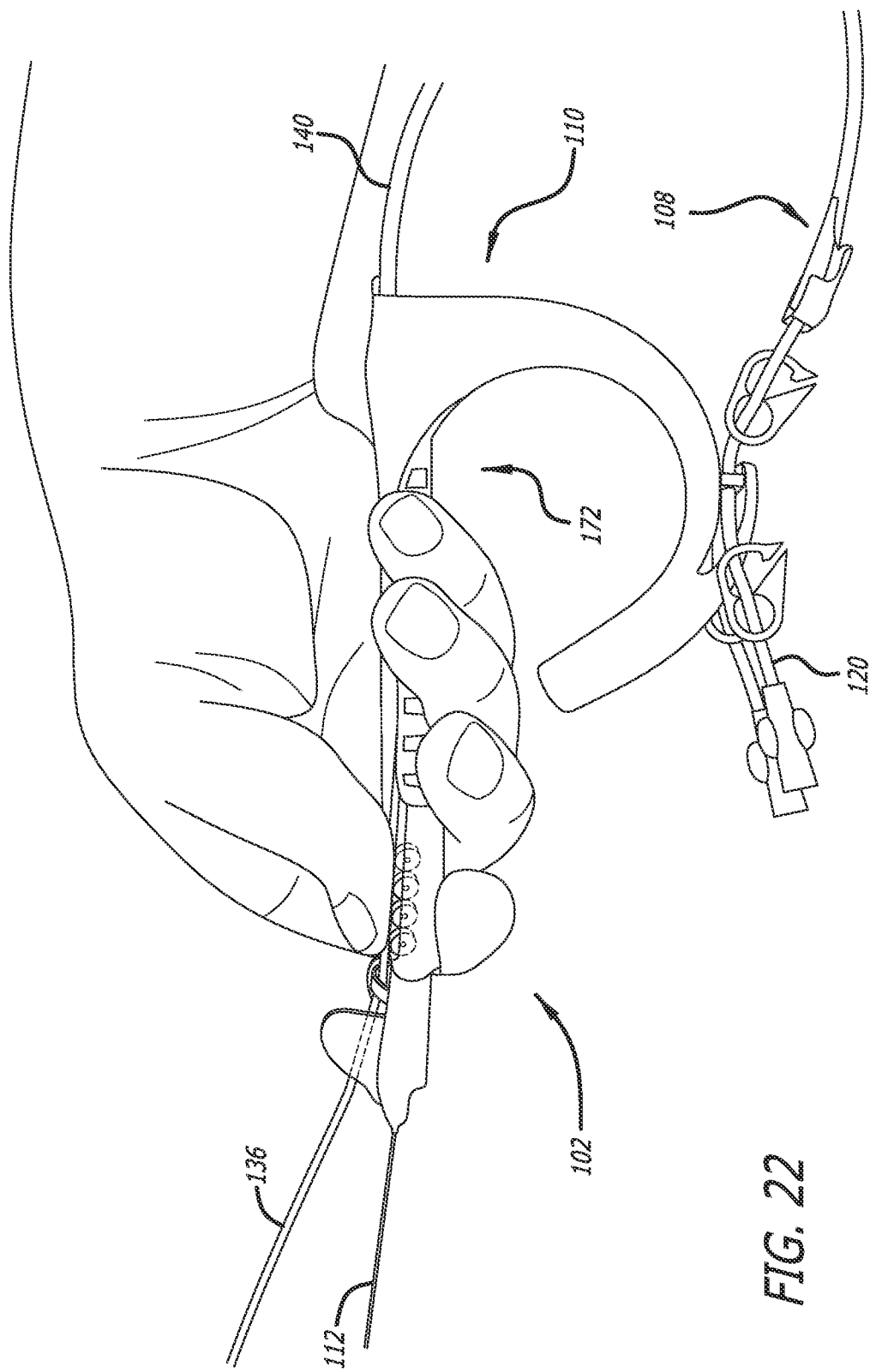

FIG. 22 provides the RICC insertion assembly with the RICC assembly in an earlier intermediate position in a frame of the RICC insertion device in accordance with some embodiments.

Figure 23B:
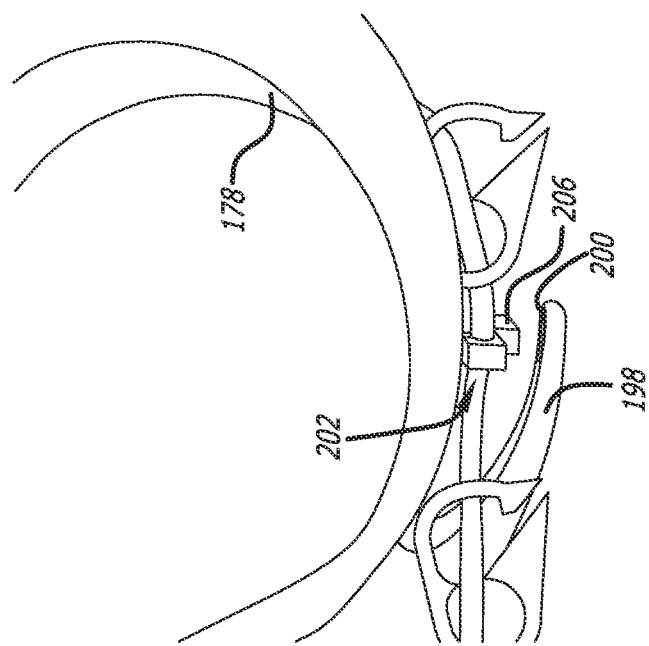
Figure 23A:
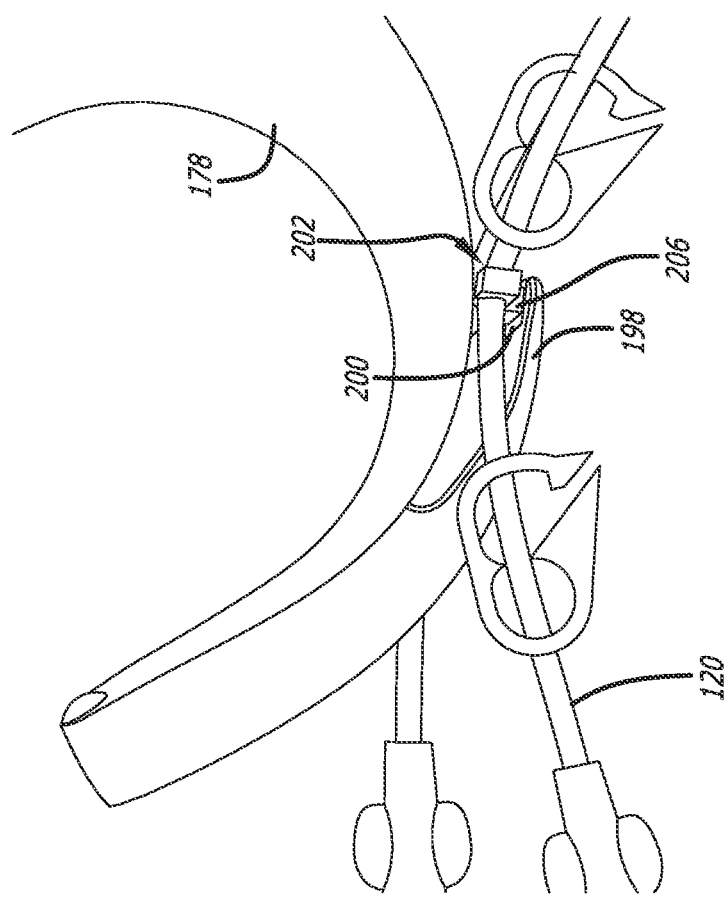

FIG. 23A provides the RICC insertion assembly with the RICC assembly in a same or different earlier intermediate position in the frame of the RICC insertion device in which a slack loop of a longitudinal composite remains in the RICC insertion assembly in accordance with some embodiments.

FIG. 23B provides the RICC insertion assembly with the RICC assembly in a later intermediate position in the frame of the RICC insertion device in which no slack loop of the longitudinal composite remains in the RICC insertion assembly in accordance with some embodiments.

Figure 24:
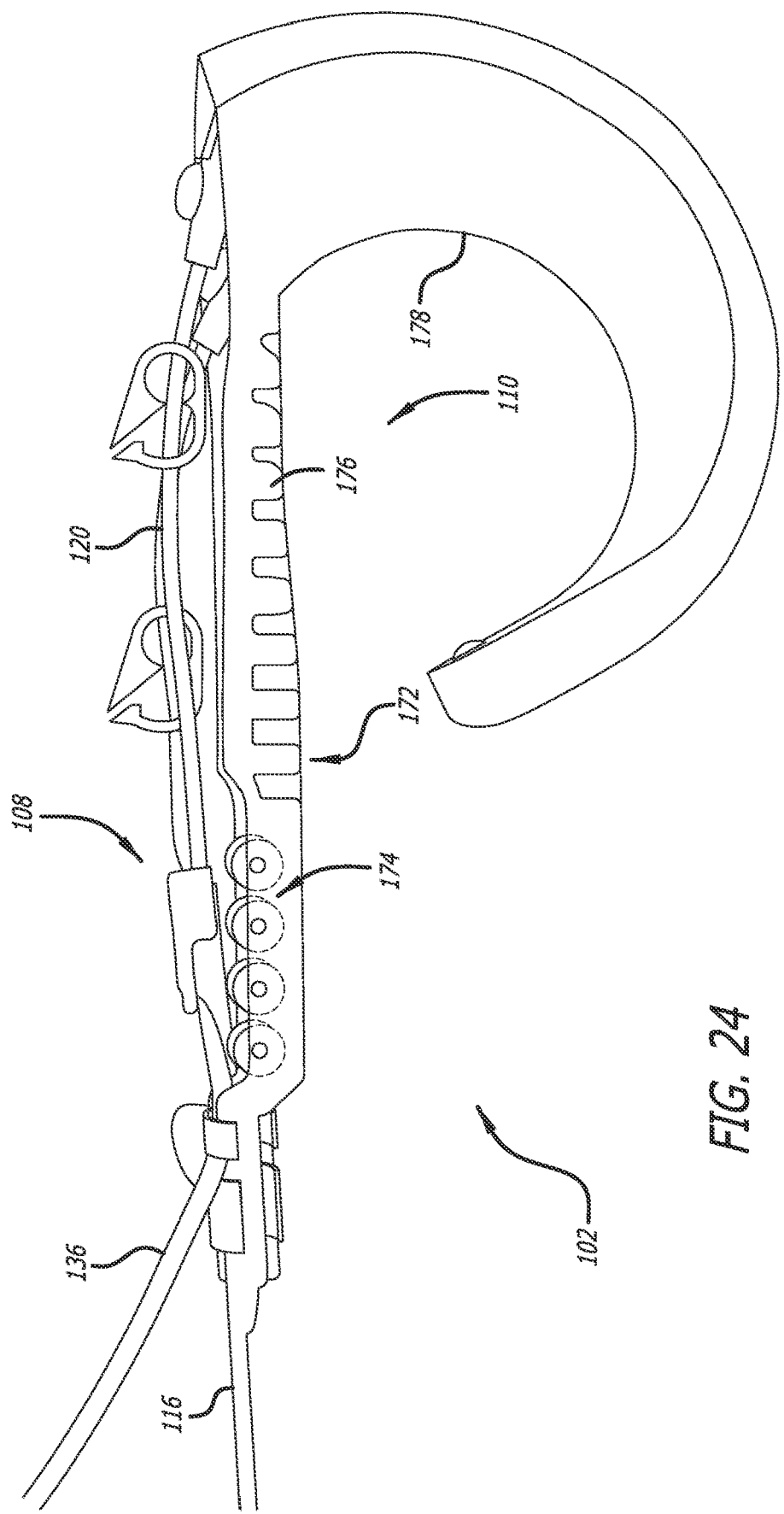

FIG. 24 provides the RICC insertion assembly with the RICC assembly in the final position in the frame of the RICC insertion device assembly in accordance with some embodiments.

Figure 25:
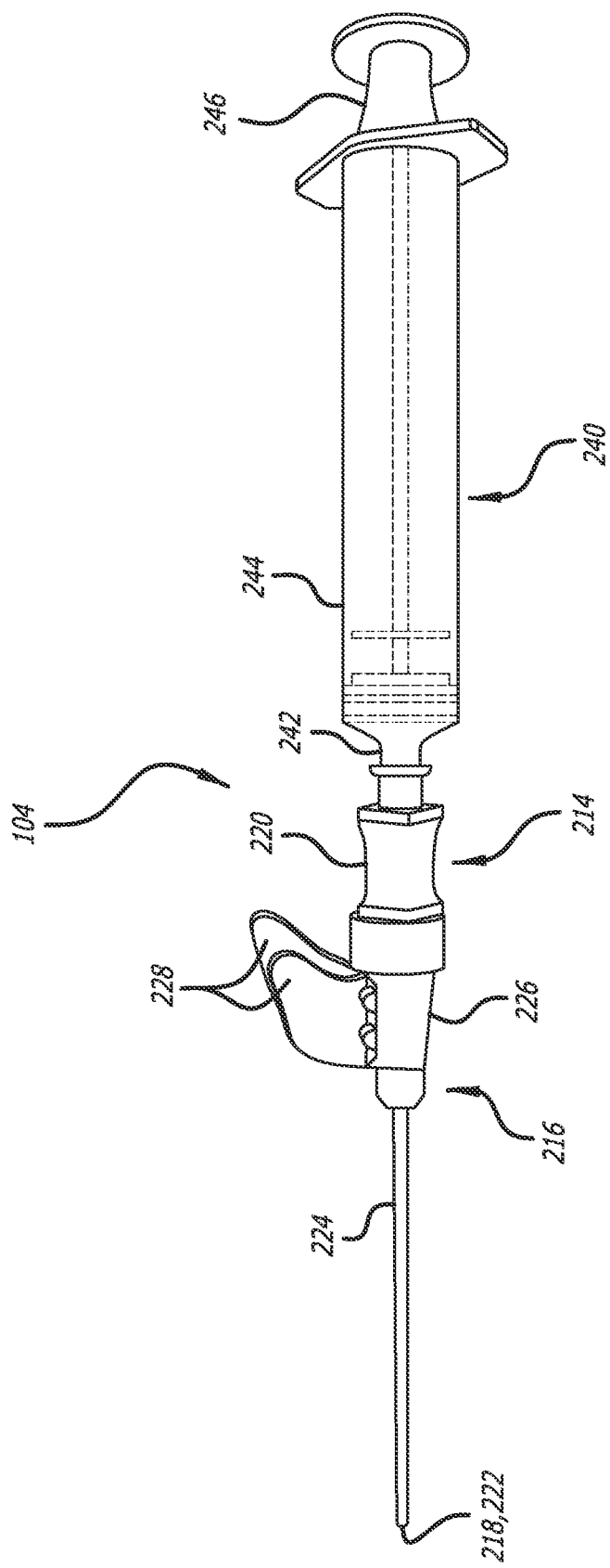

FIG. 25 provides an introducer in accordance with some embodiments.

Figure 26:
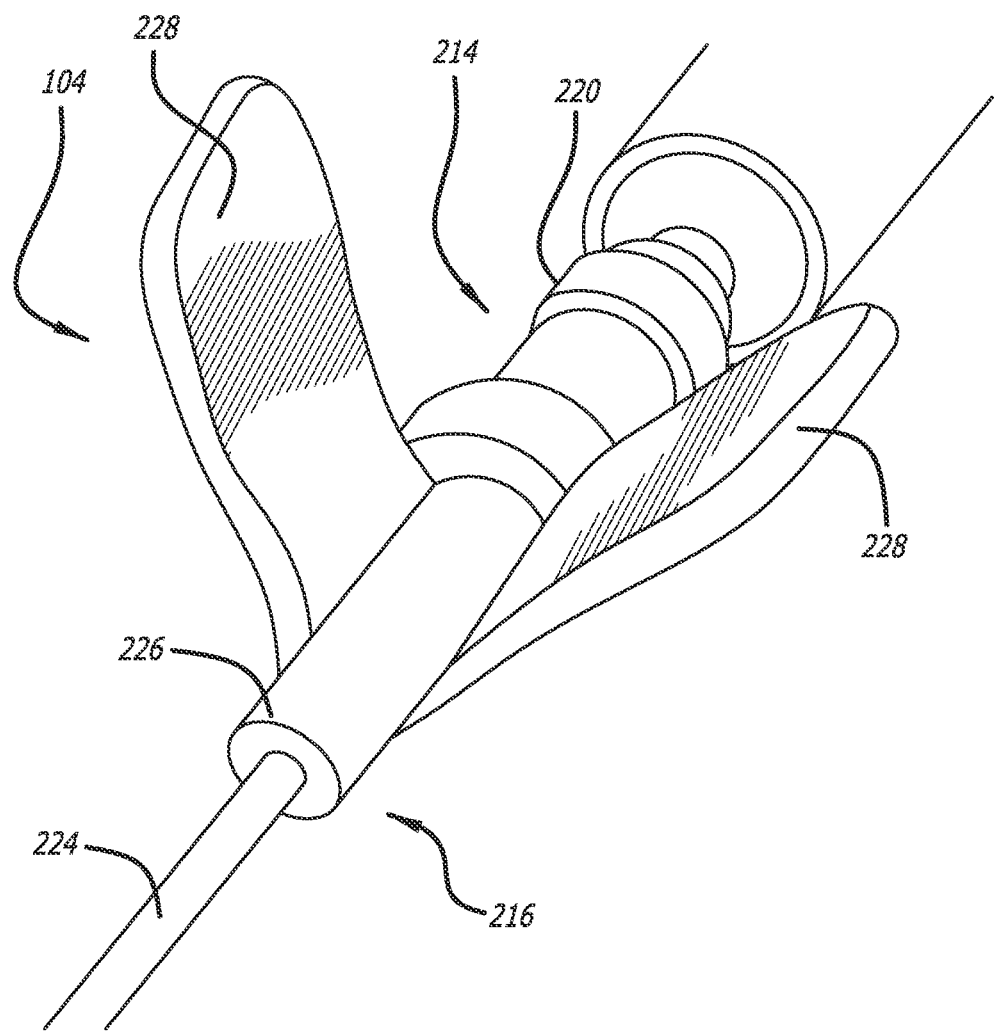

FIG. 26 provides a pair of outwardly extending wings along a length of a sheath hub of the introducer in accordance with some embodiments.

FIG. 27 provides a longitudinal cross section of the sheath hub in accordance with some embodiments.

Figure 28A:
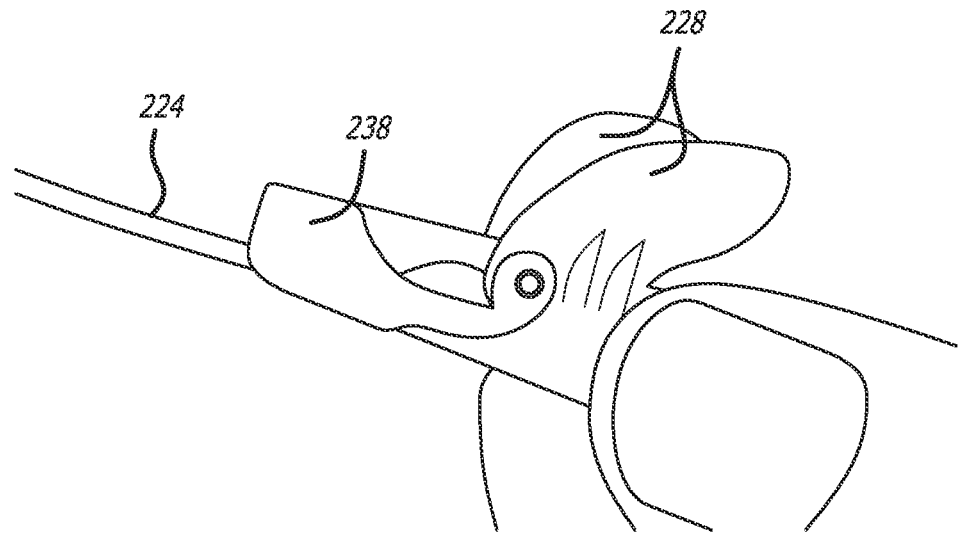

FIG. 28A provides an overmolded nicking blade integrated into the sheath hub with a nicking-blade cover in a safety position in accordance with some embodiments.

Figure 28B:
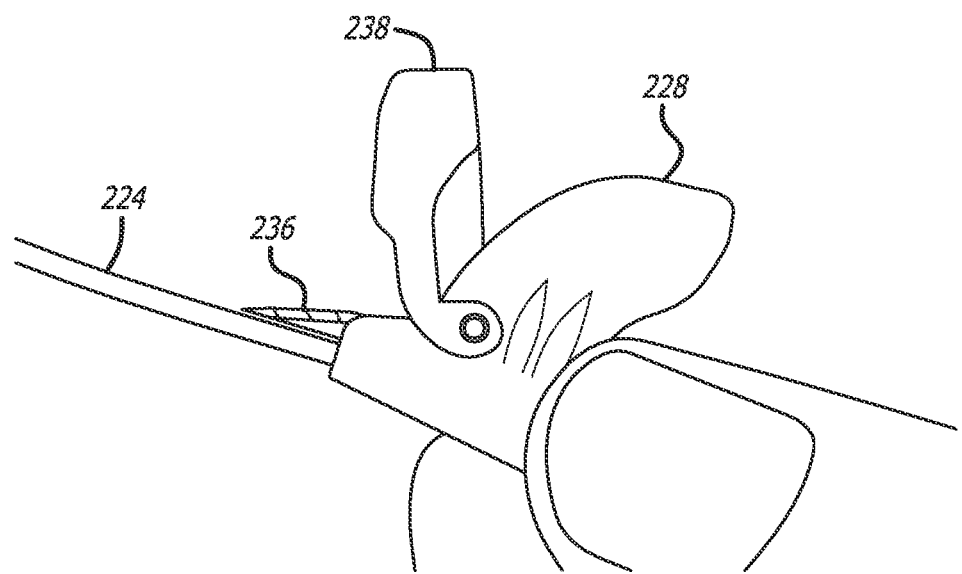

FIG. 28B provides the overmolded nicking blade integrated into the sheath hub with the nicking-blade cover in a nicking position in accordance with some embodiments.

Figure 29:
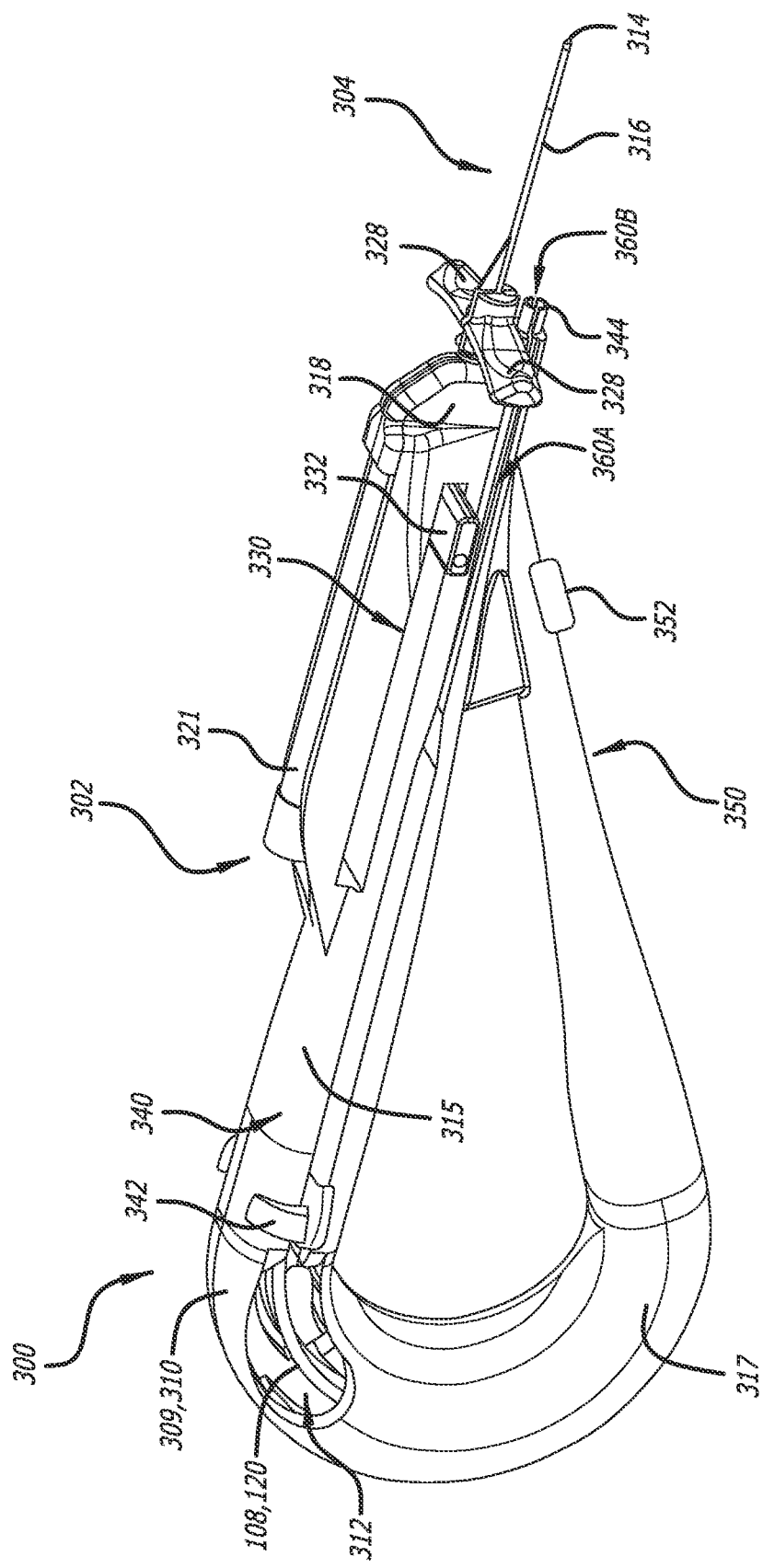

FIG. 29 provides another RICC insertion system including another RICC insertion assembly in accordance with some embodiments.

Figure 30:
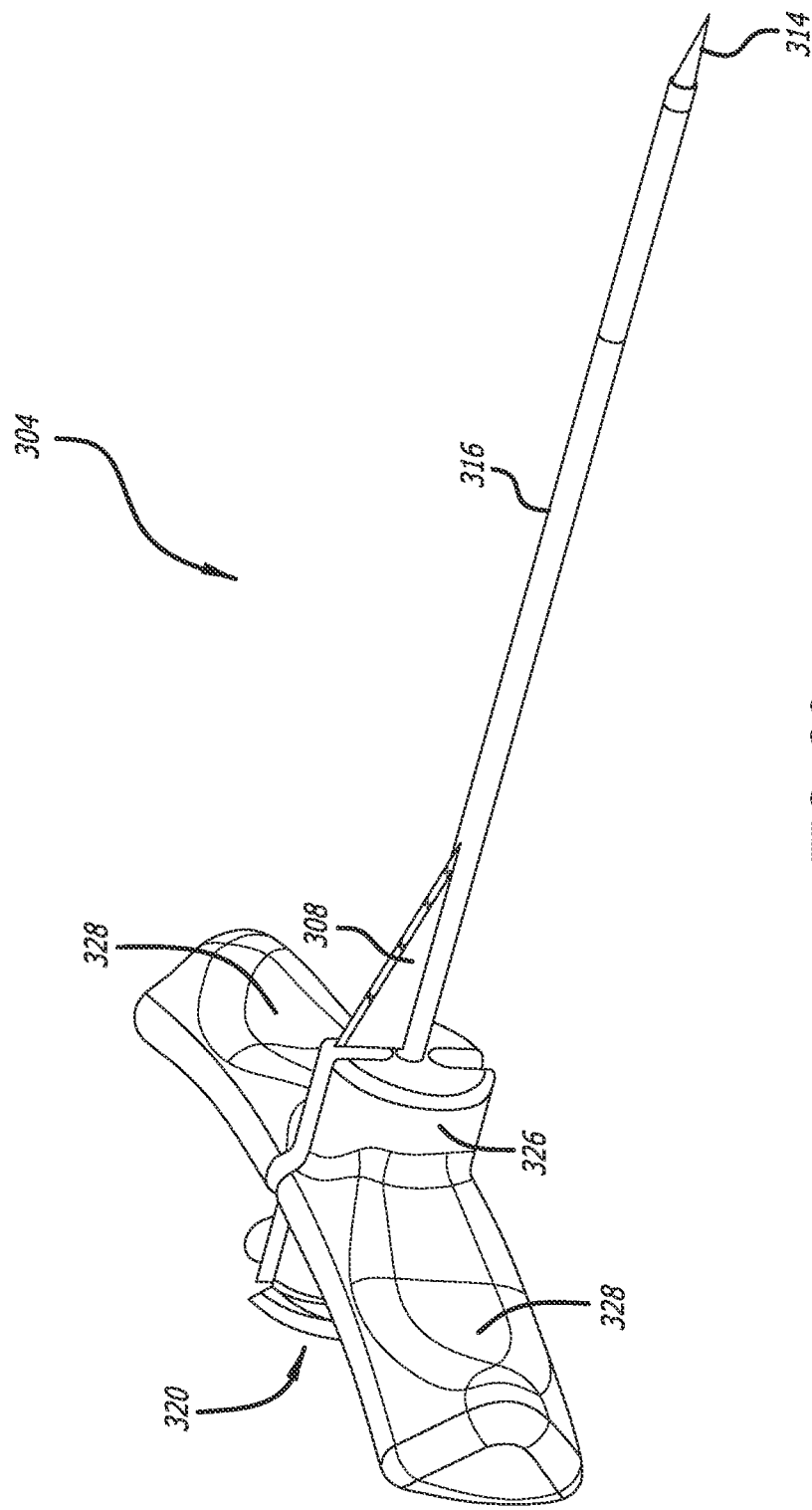

FIG. 30 provides a detailed view of an introducer of the RICC insertion assembly of FIG. 29 in accordance with some embodiments.

Figure 31:
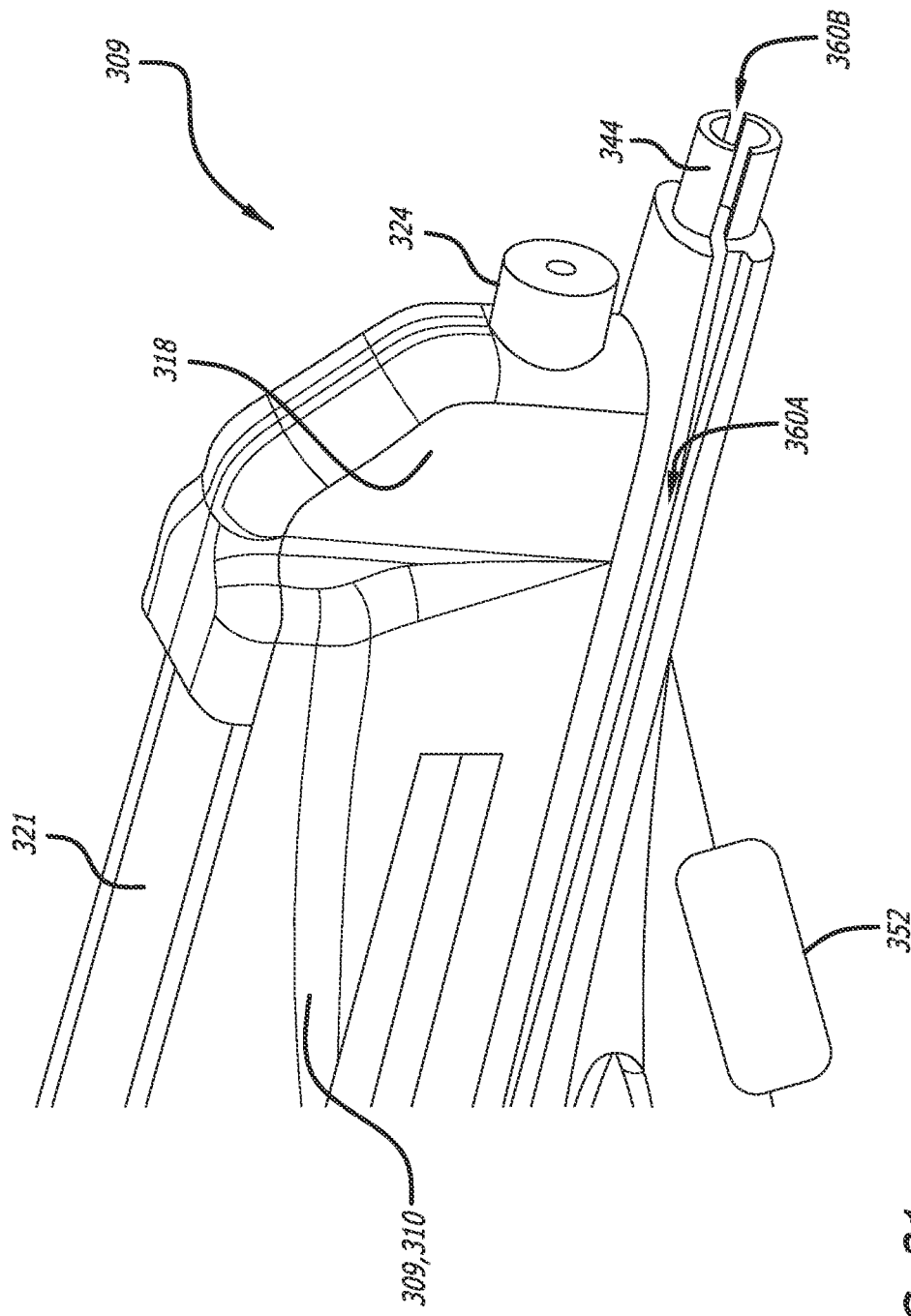

FIG. 31 provides a detailed view of a nose portion of a RICC insertion device of the RICC insertion assembly of FIG. 29 in accordance with some embodiments.

Figure 32A:
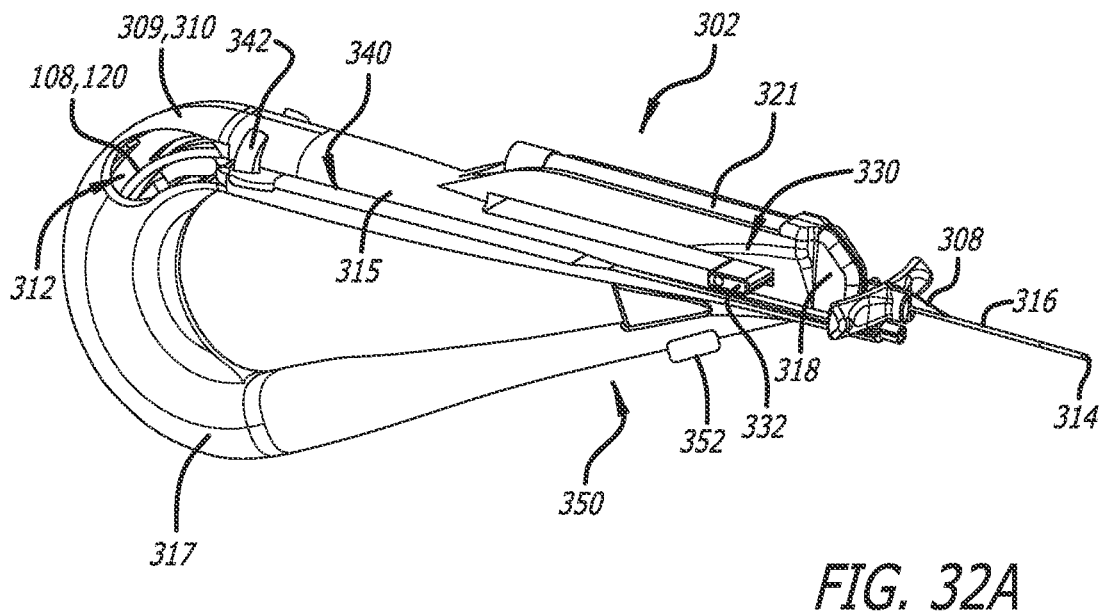

FIG. 32A provides a first state of the RICC insertion assembly of FIG. 29 in a method of using the RICC insertion system in accordance with some embodiments.

Figure 32B:
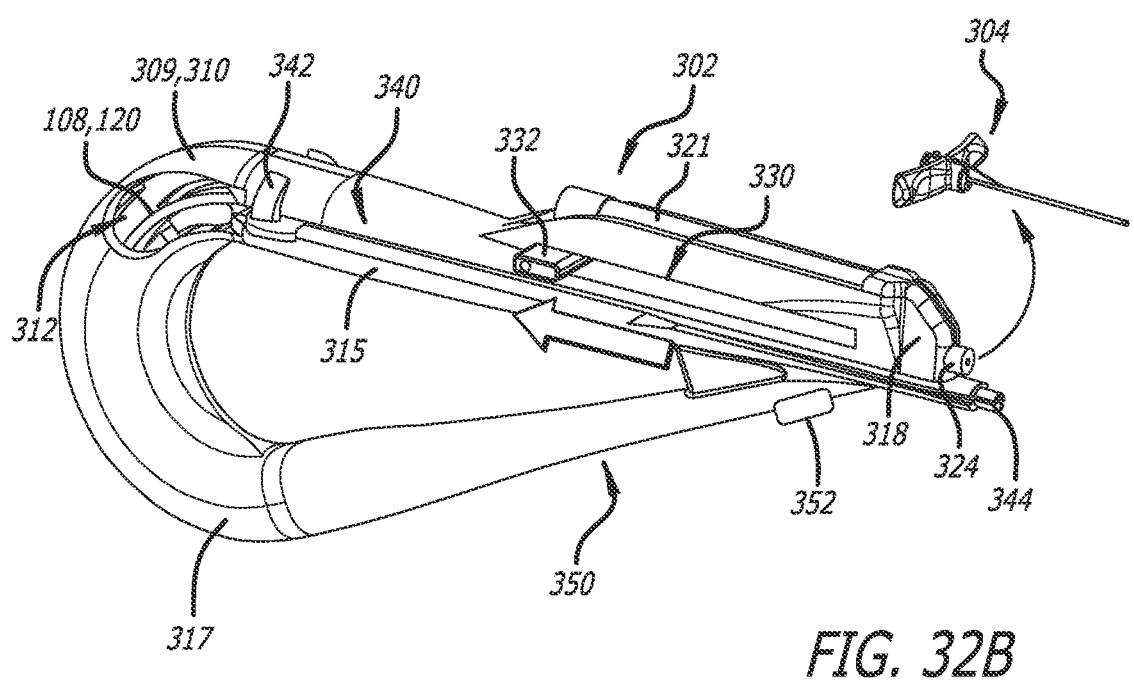

FIG. 32B provides a second state of the RICC insertion assembly of FIG. 29 in the method of using the RICC insertion system in accordance with some embodiments.

Figure 32C:
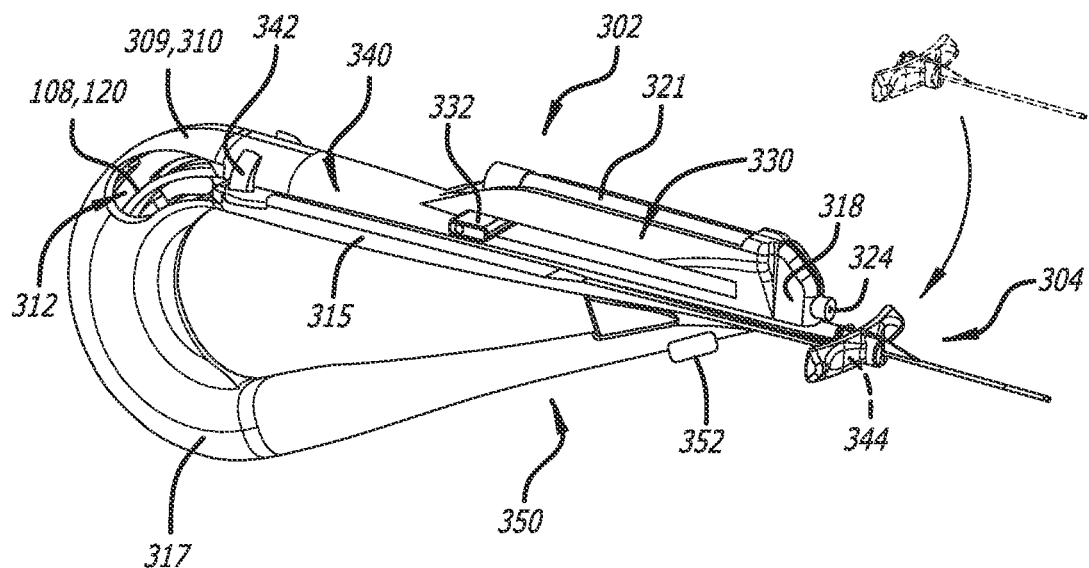

FIG. 32C provides a third state of the RICC insertion assembly of FIG. 29 in the method of using the RICC insertion system in accordance with some embodiments.

Figure 32D:
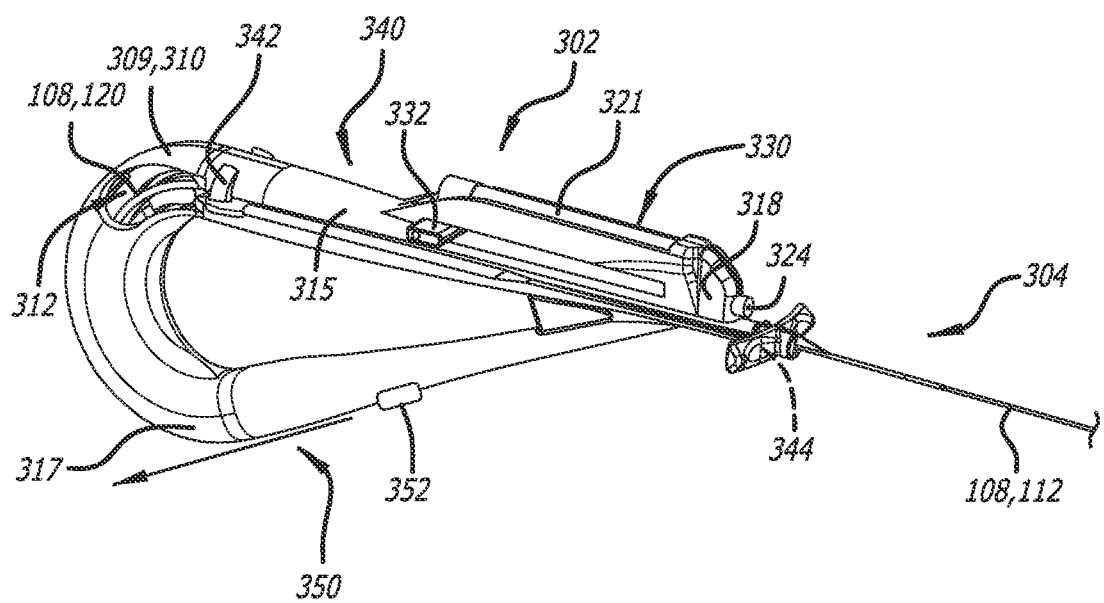

FIG. 32D provides a fourth state of the RICC insertion assembly of FIG. 29 in the method of using the RICC insertion system in accordance with some embodiments.

Figure 32E:
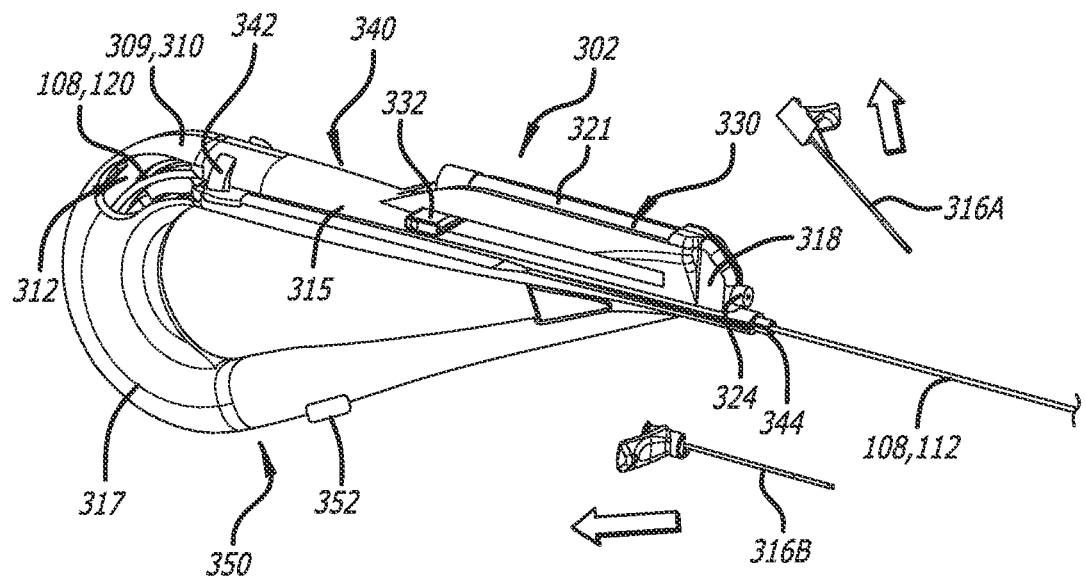

FIG. 32E provides a fifth state of the RICC insertion assembly of FIG. 29 in the method of using the RICC insertion system in accordance with some embodiments.

Figure 32F:
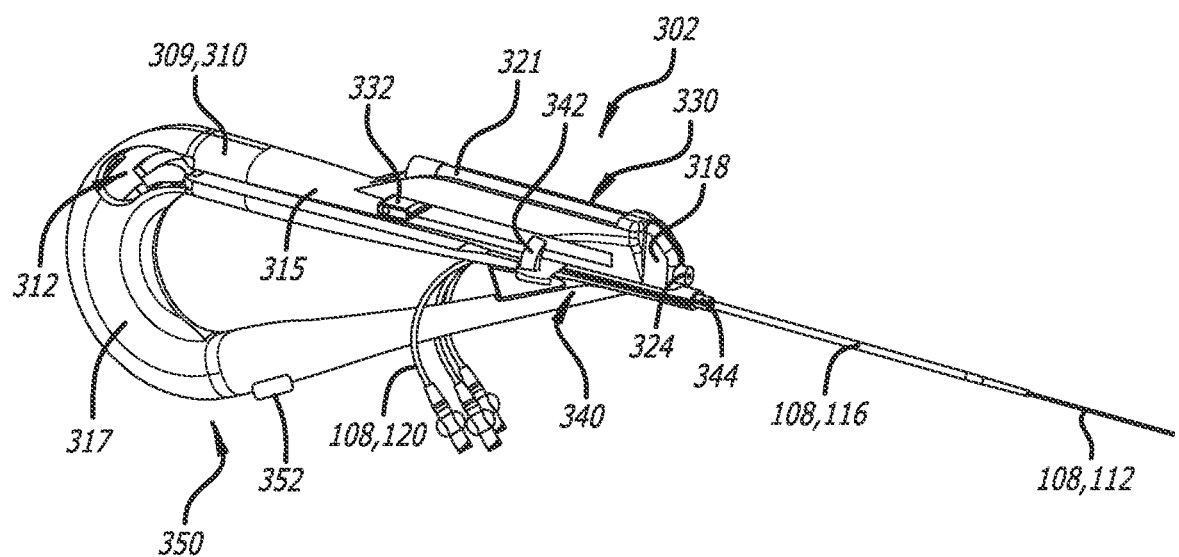

FIG. 32F provides a sixth state of the RICC insertion assembly of FIG. 29 in the method of using the RICC insertion system in accordance with some embodiments.

Figure 32G:
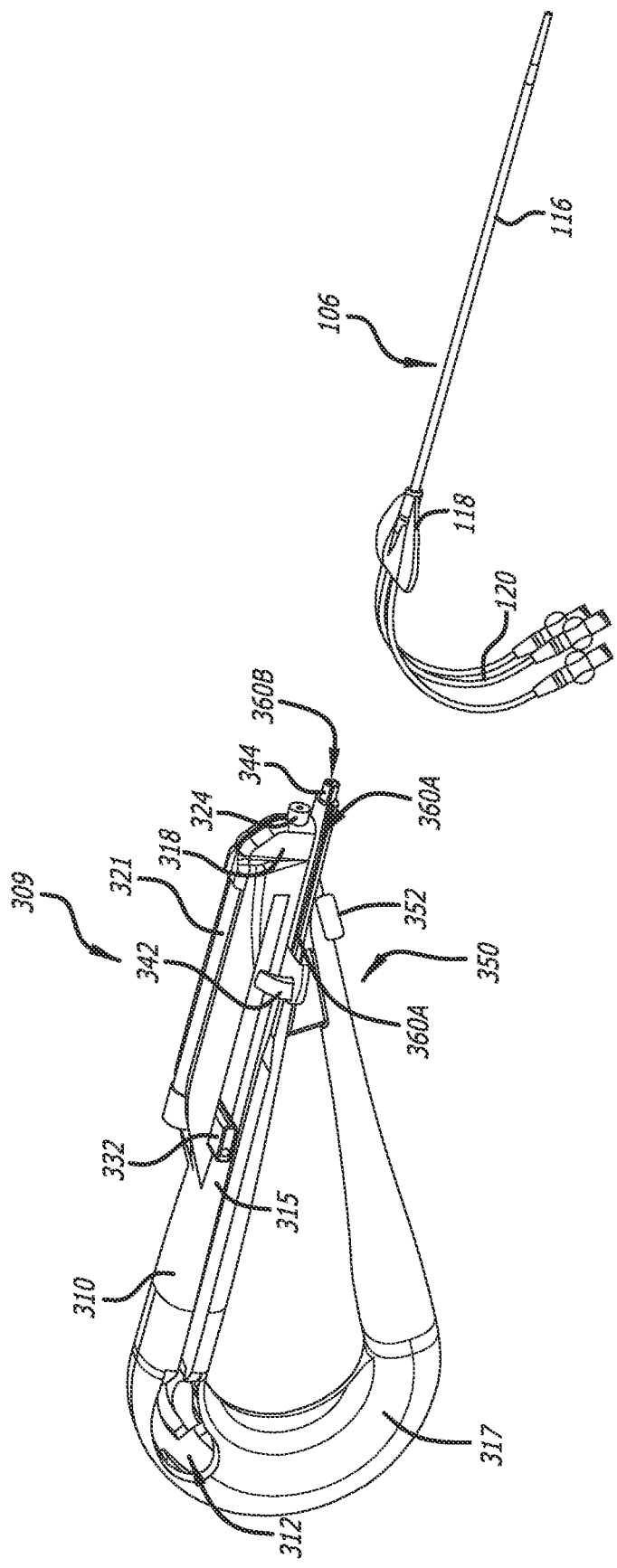

FIG. 32G provides a seventh state of the RICC insertion assembly of FIG. 29 in the method of using the RICC insertion system in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter such as a CVC into a patient and advancing the catheter through a vasculature thereof. Disclosed herein are RICCs, introducers, and insertion devices including combinations and methods thereof that address the foregoing. However, it should be understood the RICCs are but one type of catheter in which the concepts provided herein can be embodied or otherwise incorporated. Indeed, peripherally inserted central catheters ("PICCs"), dialysis catheters, or the like can also embody or otherwise incorporate the concepts provided herein for the RICCs, introducers, and insertion devices including combinations and methods thereof.

RICC Insertion Systems

FIG. 1 provides a RICC insertion system 100 including a RICC insertion assembly 102 and an introducer 104 in accordance with some embodiments.

As shown, the RICC insertion system 100 can include a RICC 106 as part of a RICC assembly 108, a RICC insertion device 110, and the introducer 104. The RICC assembly 108 can be disposed in the initial position in the frame 172 of the RICC insertion device 110 as set forth below, thereby forming a substantially ready-to-operate state of the RICC insertion assembly 102 as further shown in FIG. 1.

For convenience, description for certain components of the RICC insertion system 100 including the RICC assembly 108, the RICC insertion device 110, the RICC insertion assembly 102, and the introducer 104 is set forth below in sections named for the certain components. However, description for a component of the RICC insertion system 100 is not limited to any particular section. Indeed, description for any component of the RICC insertion system 100 can crossover from one section into one or more other sections in view of the interrelatedness of the components of the RICC insertion system 100. For example, description for the RICC assembly 108 or the RICC insertion device 110 can crossover from the section therefor into the section for the RICC insertion assembly 102. Likewise, description for the RICC insertion assembly 102 can crossover from the section therefor into the section for the RICC assembly 108 or the RICC insertion device 110. Therefore, it should be understood that description for the RICC assembly 108, the RICC insertion device 110, the RICC insertion assembly 102, the introducer 104, or any other components of the RICC insertion system 100 might be found anywhere in this patent application.

RICC Insertion Kits

While not shown, a RICC insertion kit can include the RICC insertion system 100, instructions for use of the RICC insertion system 100, and packaging. Again, the RICC insertion system 100 can include the RICC assembly 108, the RICC insertion device 110, and the introducer 104. The RICC assembly 108 can be disposed in the RICC insertion device 110 in the substantially ready-to-operate state of the RICC insertion assembly 102 for immediate use of the RICC insertion assembly 102 upon its removal from the RICC insertion kit. The RICC insertion system 100 can be packaged in the packaging (e.g., a polyethylene pouch, a polyethylene/Tyvek® pouch, etc.). The instructions for use can be either packaged in the packaging with the RICC insertion system 100 or printed on the packaging.

Notwithstanding the foregoing RICC insertion kit, a combination of components less than an entirety of the RICC insertion system 100 (i.e., the RICC assembly 108, the RICC insertion device 110, and the introducer 104) can be packaged together in some packaging with instructions for use of the combination of components or the entirety of the RICC insertion system 100 in the packaging or printed on the packaging. For example, the RICC assembly 108 and the RICC insertion device 110 can be packaged in the substantially ready-to-operate state of the RICC insertion assembly 102 with instructions for use of the RICC insertion assembly 102 or the entirety of the RICC insertion system 100 in the packaging or printed on the packaging. Each component of the RICC insertion system 100 (i.e., the RICC assembly 108, the RICC insertion device 110, and the introducer 104) can also be separately packaged in some packaging with instructions for use of the component, a combination of components including the component, or the entirety of the RICC insertion system 100 in the packaging or printed on the packaging. For example, the introducer 104 can be packaged with instructions for use of the introducer 104 or the entirety of the RICC insertion system 100 in the packaging or printed on the packaging.

RICC Assemblies

FIG. 6 provides the RICC assembly 108 in accordance with some embodiments, whereas FIGS. 9, 11, 14, 15A, and 15B provide some alternative RICC assemblies in accordance with some embodiments.

As shown, the RICC assembly 108 can include the RICC 106, an access guidewire 112, and a keeper 114. Notably, the RICC assembly 108 need not include the keeper 114 in certain embodiments such as that of FIG. 29.

FIG. 2 provides the RICC 106 in accordance with some embodiments. FIG. 3 provides a distal portion of the RICC 106, FIG. 4 provides a first transverse cross section of the distal portion of the RICC 106, and FIG. 5 provides a second or third transverse cross section of the distal portion of the RICC 106 in accordance with some embodiments.

As shown, the RICC 106 can include a catheter tube 116, a catheter hub 118, and one or more extension legs 120.

The catheter tube 116 can include a catheter tip 122 in a distal portion of the catheter tube 116 and one or more catheter-tube lumens through the catheter tube 116.

The one-or-more catheter-tube lumens can extend through an entirety of the catheter tube 116; however, only one catheter-tube lumen typically extends from a proximal end of the catheter tube 116 to a distal end of the catheter tube 116 in a multiluminal RICC (e.g., a diluminal RICC, a triluminal RICC, a tetraluminal RICC, a pentaluminal RICC, a hexaluminal RICC, etc.). (See FIGS. 3-5.) Indeed, the catheter tip 122, typically includes a single lumen therethrough, whether or not the catheter tip 122 is formed integrally with the catheter tube 116 or separately from the catheter tube 116 and coupled thereto.

The catheter hub 118 can be coupled to a proximal portion of the catheter tube 116. The catheter hub 118 can include one or more catheter-hub lumens corresponding in number to the one-or-more catheter-tube lumens. The one-or-more catheter-hub lumens can extend through an entirety of the catheter hub 118 from a proximal end of the catheter hub 118 to a distal end of the catheter hub 118.

Each extension leg of the one-or-more extension legs 120 can be coupled to the catheter hub 118 by a distal portion thereof. The one-or-more extension legs 120 can respectively include one or more extension-leg lumens, which, in turn, correspond in number to the one-or-more catheter-hub lumens. Each extension-leg lumen of the one-or-more extension-leg lumens can extend through an entirety of the extension leg from a proximal end of the extension leg to a distal end of the extension leg.

Each extension leg of the one-or-more extension legs 120 can include a Luer connector coupled to the extension leg, through which Luer connector the extension leg and the extension-leg lumen thereof can be connected to another medical device and a lumen thereof.

As shown, the RICC 106 can be a triluminal RICC including a set of three lumens. The set of three lumens can include a primary lumen 124, a secondary lumen 126, and a tertiary lumen 128 formed of fluidly connected portions of three catheter-tube lumens, three catheter-hub lumens, and three extension-leg lumens. The primary lumen 124 can have a primary-lumen aperture 130 in a distal end of the catheter tip 122, the distal end of the catheter tube 116, or a distal end of the RICC 106. The secondary lumen 126 can have a secondary-lumen aperture 132 in a side of the distal portion of the catheter tube 116. The tertiary lumen 128 can have a tertiary-lumen aperture 134 in the side of the distal portion of the catheter tube 116 proximal of the secondary-lumen aperture 132.

The access guidewire 112 can be disposed in the primary lumen 124 of the RICC 106 in the RICC assembly 108. The access guidewire 112 can include a distal portion extending from the distal end of the RICC 106 as evidenced by comparison of at least FIGS. 7 and 8. The access guidewire 112 can also include a proximal portion extending from a proximal end of the RICC 106 as shown in FIG. 6. As set forth below, the proximal portion of the access guidewire 112 extending from the proximal end of the RICC 106 or a guidewire hub 135 coupled thereto can be attached to the guidewire attachment point 196 in the closed end of the enclosure 192 in the initial position of the RICC assembly 108 in the frame 172.

The keeper 114 can include a splittable casing 136 and a catheter-hub holder 138 to which a proximal end of the splittable casing 136 is attached.

FIGS. 7 and 8 provide transverse cross sections of the RICC assembly 108, which, in turn, provide the splittable casing 136 as part of a longitudinal composite 140 of the RICC assembly 108 in accordance with some embodiments.

As shown, the splittable casing 136 can form the longitudinal composite 140 with the catheter tube 116, the access guidewire 112, or both the catheter tube 116 and the access guidewire 112 in the RICC assembly 108 depending upon the embodiment of the RICC assembly 108 and portion thereof. With respect to the RICC assembly 108 of FIG. 6, for example, the splittable casing 136 can be over both the catheter tube 116 and the access guidewire 112 in a proximal portion of the RICC assembly 108 as shown in FIG. 7. The splittable casing 136 can also be over the distal portion of the access guidewire 112 extending from the distal end of the RICC 106 as shown in FIG. 8. The splittable casing 136 is configured to split along its length such that the distal portion of the access guidewire 112 is initially revealed and the distal portion of the catheter tube 116 is subsequently revealed. In this way, the splittable casing 136 is configured to keep the catheter tube 116 and at least the distal portion of the access guidewire 112 sterile until deployed.

The catheter-hub holder 138 is configured to hold the catheter hub 118 therein as well as keep the splittable casing 136 in position over the catheter tube 116 and the access guidewire 112. The catheter-hub holder 138 includes a perimetrical wall 142 around at least a portion (e.g., a proximal portion) of a perimeter of the catheter-hub holder 138. The perimetrical wall 142 defines a recess into which the catheter hub 118 fits with an engineering fit (e.g., a clearance fit such as a running, sliding, or location fit or a transition fit such as a similar or fixed fit as classified by the International Organization for Standardization ["ISO"]) as well as one or more gaps 144 for extension of the one-or-more extension legs 120 therethrough. Additionally or alternatively, the catheter-hub holder 138 can include a wing corresponding to a suture wing 146 of the catheter hub 118. Such a wing can include posts configured to insert into suture-wing holes 148 of the suture wing 146 of the catheter hub 118 with an engineering fit.

FIG. 9 provides a first alternative RICC assembly 150 in accordance with some embodiments. FIG. 10 provides a transverse cross section of the RICC assembly 150 in accordance with some embodiments.

As shown, the RICC assembly 150 can include the RICC 106, the access guidewire 112, and the keeper 114; however, the splittable casing 136 over the catheter tube 116 and the access guidewire 112 can have a larger diameter over the catheter tube 116 and a smaller diameter over the access guidewire 112, thereby more closely following contours of the catheter tube 116 and the access guidewire 112. Advantageously, the splittable casing 136 can keep the catheter tube 116 from prematurely advancing over the access guidewire 112 while advancing the RICC assembly 150 from the initial position in the frame 172 to the final position in the frame 172 as set forth below.

FIG. 11 provides a second alternative RICC assembly 152 in accordance with some embodiments. FIG. 12 provides a first transverse cross section of the RICC assembly 152 in accordance with some embodiments. FIG. 13 provides a second transverse cross section of the RICC assembly 152 in accordance with some embodiments.

As shown, the RICC assembly 152 can include the RICC 106 and the access guidewire 112 without the keeper 114 and the splittable casing 136 thereof. Optionally, the catheter tube 116 and the access guidewire 112 can be disposed in a clear covering such as a collapsible plastic bag configured to keep the catheter tube 116 and the distal portion of the access guidewire 112 sterile until deployed. Whether the catheter tube 116 and the access guidewire 112 are bare or disposed in the covering, a transition between the distal portion of the access guidewire 112 and the catheter tube 116 can be advantageously visualized while advancing the RICC assembly 152 from the initial position in the frame 172 to the final position in the frame 172 as set forth below.

FIG. 14 provides a third alternative RICC assembly 154 in accordance with some embodiments.

As shown, the RICC assembly 154 can include the RICC 106 and the access guidewire 112 without the keeper 114 and the splittable casing 136 thereof. Instead of the optional covering over the catheter tube 116 and the access guidewire 112 of the RICC assembly 152, an entirety of the RICC assembly 154 can be disposed a clear covering 156 such as a collapsible or zippered plastic bag configured to keep the catheter tube 116 and the distal portion of the access guidewire 112 sterile until deployed. Like the RICC assembly 152, the transition between the distal portion of the access guidewire 112 and the catheter tube 116 can be advantageously visualized through the covering 156 while advancing the RICC assembly 154 from the initial position in the frame 172 to the final position in the frame 172 as set forth below.

FIGS. 15A and 15B provide different views of a fourth alternative RICC assembly 158 in accordance with some embodiments.

As shown, the RICC assembly 158 can include the RICC 106 and the access guidewire 112 without the keeper 114 and the splittable casing 136 thereof; however, the RICC assembly 158 including the catheter tube 116 and the distal portion of the access guidewire 112 can be disposed in a longitudinal housing 160 with the proximal portion of the access guidewire 112 extending therefrom but disposed in a clear covering 162 such as a collapsible plastic bag. The housing 160 can include longitudinal slots 164 configured for advancing or withdrawing a RICC-advancement wing 166 therein. The RICC-advancement wing 166 can be configured like the catheter-hub holder 138 such that the catheter hub 118 fits in the RICC-advancement wing 166 with an engineering fit or the suture wing 146 thereof fits over posts of the RICC-advancement wing 166. Regardless, the housing 160 can be configured to keep the catheter tube 116 and the distal portion of the access guidewire 112 sterile until deployed. Advantageously, the housing 160 can prevent the guidewire hub 135 of the access guidewire 112 from passing into the housing 160, thereby controlling relative movement of the catheter tube 116 and the access guidewire 112.

RICC Insertion Devices

FIG. 16 provides the RICC insertion assembly 102 including the RICC assembly 108 disposed in the RICC insertion device 110 in accordance with some embodiments. FIG. 17 provides a nose cover 168 over a nose 170 of a frame 172 of the RICC insertion device 110 in accordance with some embodiments.

As shown, the RICC insertion device 110 can include the frame 172, one or more roller wheels 174, and the nose cover 168 over the nose 170 of the frame 172. The RICC insertion device 110 can be configured for advancing the RICC assembly 108 from an initial position in the frame 172, (see FIG. 16) through one or more intermediate positions in the frame 172, (see FIG. 22) to a final position in the frame 172 (see FIG. 24) for insertion of the access guidewire 112 and the catheter tube 116 of the RICC 106 into a blood-vessel lumen of a patient subsequent to establishment of a needle tract to the blood-vessel lumen.

The frame 172 can include a longitudinal handle 176, the nose 170, and a curved cradle 178; however, in some embodiments, the cradle 178 can be a reel.

The handle 176 can include a wheel well 180 in a distal portion of the handle 176. The wheel well 180, in turn, can include the one-or-more roller wheels 174 disposed therein. The handle 176 can be configured for holding and operating the RICC insertion device 110 with a single hand (e.g., a left or right hand). For example, when the RICC assembly 108 is disposed in the RICC insertion device 110, the RICC assembly 108 can be advanced from the initial position in the frame 172, through the one-or-more intermediate positions in the frame 172, to the final position in the frame 172 with a single hand by repeatedly pushing the longitudinal composite 140 of the RICC assembly 108 into the one-or-more roller wheels 174 and rolling the longitudinal composite 140 across the one-or-more roller wheels 174 with a thumb of the hand while cradling the handle 176 of the RICC insertion device 110 in fingers of the same hand.

The nose 170 can be integral with the handle 176, extending from the distal portion of the handle 176 distal of the wheel well 180. The nose 170 can include a through channel 182 configured for advancing the access guidewire 112 and the catheter tube 116 of the RICC assembly 108 therethrough. Together, the nose 170 and the nose cover 168 thereover can form a split channel 184 configured for both splitting and passing the splittable casing 136 of the RICC assembly 108 therethrough. Advantageously, the nose 170 can also include a male nose connector 186 configured to be disposed in the female valved-cap connector 232 of the sheath hub 226 of the introducer sheath 216 set forth below, which facilitates advancing the access guidewire 112 through the introducer sheath.

FIG. 18A and FIG. 18B provide a retaining clamp 188 formed between the nose 170 and the nose cover 168 with the retaining clamp 188 respectively in a closed state and an open state in accordance with some embodiments.

As shown, the nose 170 and the nose cover 168 thereover can also form the retaining clamp 188. The retaining clamp 188 can be configured to slidably clamp therein the longitudinal composite 140 of the RICC assembly 108 or the splittable casing 136, the catheter tube 116, or the access guidewire 112 thereof. The nose cover 168 can be rotatable over the nose 170. In addition, the nose cover 168 can include a longitudinal gap 190 configured to rotatably align with the through channel 182 in the nose 170 for removal of the longitudinal composite 140 of the RICC assembly 108 or the splittable casing 136, the catheter tube 116, or the access guidewire 112 therefrom. Indeed, if the longitudinal composite 140 is partially or fully split, the longitudinal gap 190 of the nose cover 168 can be rotatably aligned with the through channel 182 in the nose 170 for removal of the splittable casing 136, the catheter tube 116, or the access guidewire 112 therefrom.

The cradle 178 can be integral with the handle 176, extending from a proximal portion of the handle 176 and curving back toward the distal portion of the handle 176. The cradle 178 can include an open face, an enclosure 192 over a distal portion of the cradle 178, and a retaining arch 194 over the cradle 178 proximate the proximal portion of the handle 176 from which the cradle 178 extends.

The open face of the cradle 178 can be configured for cradling therein the RICC assembly 108 (e.g., the longitudinal composite 140, the catheter hub 118, the one-or-more extension legs 120, etc.) from the initial position of the RICC assembly 108 in the frame 172, through the one-or-more intermediate positions of the RICC assembly 108 in the frame 172, to the final position of the RICC assembly 108 in the frame 172.

The enclosure 192 over the cradle 178 can be configured to enclose therein the otherwise exposed proximal portion of the access guidewire 112 as well the extension leg of the one-or-more extension legs 120 from which the proximal portion of the access guidewire 112 extends in the initial position of the RICC assembly 108 in the frame 172. (See FIGS. 16, 22, and 23A.) Indeed, the foregoing proximal portion of the access guidewire 112 or the guidewire hub 135 coupled thereto can be attached to a guidewire attachment point 196 in a closed end of the enclosure 192 in the initial position of the RICC assembly 108 in the frame 172. In this way, the enclosure 192 can keep at least the proximal portion of the access guidewire 112 extending from the proximal end of the RICC 106 touch-free and sterile.

The retaining arch 194 over the cradle 178 is configured to retain the RICC assembly 108 in the RICC insertion device 110. The retaining arch 194 is also configured to hold the longitudinal composite 140 over the handle 176 as the RICC assembly 108 transitions over the proximal portion of the handle 176 from which the cradle 178 extends upon advancing the RICC assembly 108 from the initial position to the final position in the frame 172.

FIG. 19 provides a curved extension 198 of the cradle 178 extending from the enclosure 192 in accordance with some embodiments.

As shown, the extension 198 can extend from an open end of the enclosure 192 over the distal portion of the cradle 178 substantially following a same curve as the cradle 178. The extension 198 can include a slot 200 in the extension 198 that faces the open face of the cradle 178. As set forth below, the slot 200 can be configured to engage with the retaining clip 202.

FIG. 20 provides a retaining clip 202 of the RICC insertion device 110 in accordance with some embodiments.

As shown, the retaining clip 202 can be a separate piece of the RICC insertion device 110 including one or more extension-leg clips 204 and a post 206. The retaining clip 202 can be configured to clip on to the proximal portion of the RICC 106 and retain the RICC assembly 108 in the RICC insertion device 110. More specifically, the retaining clip 202 can be configured to retain the RICC 106, itself, in position in the RICC insertion device 110, which, in turn, can help keep the RICC 106 and the catheter tube 116 thereof from prematurely advancing over the access guidewire 112 when advancing the RICC assembly 108 in the frame 172.

The one-or-more extension-leg clips 204 can be configured to clip on to the one-or-more extension legs 120. While the one-or-more extension-leg clips 204 can include a dedicated extension-leg clip for each extension leg of the one-or-more extension legs 120 as shown, the one-or-more extension-leg clips 204 can alternatively include a single extension-leg clip configured to clip on to any single extension leg of two or more of the extension legs 120, a pair of the extension-leg clips 204 configured to clip on to any two extension legs of three or more of the extension legs 120, etc.

The post 206 can be configured to engage with the slot 200 in the extension 198 of the cradle 178 in the initial position of the RICC assembly 108 in the frame 172 as well as through some earlier intermediate positions of the one-or-more intermediate positions of the RICC assembly 108 in the frame 172. (See FIGS. 16, 22, and 23A.) However, the retaining clip 202 can be configured to disengage with the slot 200 in the extension 198 when any remaining slack of the slack loop 212 of the longitudinal composite 140 is removed in the RICC insertion assembly 102 upon advancing the RICC assembly 108 through a transition to a later intermediate position of the one-or-more intermediate positions of the RICC assembly 108 in the frame 172. (See FIG. 23B.) The retaining clip 202 can be configured to remain clipped on the one-or-more extension legs 120 through the transition and follow the cradle 178 over the proximal portion of the handle 176 to a medial portion of the handle 176 in the final position of the RICC assembly 108 in the frame 172. (See FIG. 24.)

FIGS. 21A and 21B provide a retractable nicking blade 208 integrated into the nose 170 of the RICC insertion device 110 with the nicking blade 208 respectively in a safety position and a nicking position in accordance with some embodiments.

As shown, the nicking blade 208 can be disposed or overmolded in a nicking-blade carriage 210 slidably integrated into the nose 170. When the nicking-blade carriage 210 is in the safety position, the nicking blade 208 can be short of a distal end of the nose 170 to prevent inadvertent nicking; however, when the nicking-blade carriage 210 is in the nicking position, the nicking blade 208 can extend beyond the distal end of the nose 170 for nicking an area of skin. Notably, the nicking blade 208 can be configured for nicking the area of skin around a needle tract for subsequent insertion of the catheter tube 116 when the catheter tube 116 is 7 Fr or larger.

RICC Insertion Assemblies

Again, FIG. 16 provides the RICC insertion assembly 102 including the RICC assembly 108 disposed in the initial position in the frame 172 of the RICC insertion device 110, thereby forming the ready-to-operate state of the RICC insertion assembly 102 in accordance with some embodiments.

The RICC insertion assembly 102, which includes the RICC assembly 108 disposed in the RICC insertion device 110, can be configured for advancing the RICC assembly 108 from the initial position in the frame 172 of the RICC insertion device 110, through the one-or-more intermediate positions in the frame 172, to the final position in the frame 172 for insertion of the access guidewire 112 and the catheter tube 116 of the RICC 106 into a blood-vessel lumen of a patient subsequent to establishment of a needle tract to the blood-vessel lumen.

In the initial position of the RICC assembly 108 in the frame 172 of the RICC insertion device 110, a distal end of the longitudinal composite 140 can be substantially commensurate with a distal end of the frame 172 (e.g., the nose 170) if the longitudinal composite 140 is not split. If the longitudinal composite 140 is partially split as shown in FIG. 16, a distal end of the splittable casing 136 or the distal end of the access guidewire 112 can be substantially commensurate with the distal end of the frame 172 in the initial position of the RICC assembly 108 in the frame 172. Regardless, the retaining clamp 188 of the RICC insertion device 110 can clamp therein a distal portion of the longitudinal composite 140 in the initial position of the RICC assembly 108 in the frame 172. Further in the initial position of the RICC assembly 108 in the frame 172, a proximal end of an extension leg of the one-or-more extension legs 120 or a Luer connector coupled to the extension leg can be substantially commensurate with a proximal end of the cradle 178 of the RICC insertion device 110. In addition, a proximal end of the access guidewire 112 or the guidewire hub 135 thereof can be coupled to the proximal end of the cradle 178 (e.g., the guidewire attachment point 196 in the closed end of the enclosure 192) in the initial position of the RICC assembly 108 in the frame 172. As a result of clamping the distal portion of the longitudinal composite 140 with the retaining clamp 188 and attaching the proximal end of the access guidewire 112 or the guidewire hub 135 thereof to the proximal end of the cradle 178, a slack loop 212 of the longitudinal composite 140 can extend away from both the handle 176 and the cradle 178 in the initial position of the RICC assembly 108 in the frame 172.

FIG. 22 provides the RICC insertion assembly 102 with the RICC assembly 108 in an earlier intermediate position in the frame 172 of the RICC insertion device 110 in accordance with some embodiments. FIG. 23A provides the RICC insertion assembly 102 with the RICC assembly 108 in a same or different earlier intermediate position in the frame 172 than FIG. 22 in which the slack loop 212 of the longitudinal composite 140 remains in the RICC insertion assembly 102 in accordance with some embodiments. FIG. 23B provides the RICC insertion assembly 102 with the RICC assembly 108 in a later intermediate position in the frame 172 in which no slack loop of the longitudinal composite 140 remains in the RICC insertion assembly 102 in accordance with some embodiments.

As shown, in an earlier intermediate position of the RICC assembly 108 in the frame 172 of the RICC insertion device 110, the slack loop 212 of the longitudinal composite 140 can remain in the RICC insertion assembly 102 and extend away from both the handle 176 and the cradle 178 of the RICC insertion device 110. In addition, the post 206 of the retaining clip 202 can remain engaged with the slot 200 in the extension 198 over the cradle 178, thereby retaining the RICC 106, itself, in position in the RICC insertion device 110 such that the catheter tube 116 cannot prematurely advance over the access guidewire 112 when advancing the RICC assembly 108 in the frame 172. However, the retaining clip 202 can be configured to disengage with the slot 200 in the extension 198 when any remaining slack of the longitudinal composite 140 is removed in the RICC insertion assembly 102 upon advancing the RICC assembly 108 through the transition to a later intermediate position. Indeed, when the remaining slack of the longitudinal composite 140 is removed from the RICC insertion assembly 102, the post 206 of the retaining clip 202 can disengage with the slot 200 in the extension 198 such as by being pulled out of the slot 200, thereby allowing the RICC 106 to advance over the access guidewire 112 with advancement of the longitudinal composite 140. In the later intermediate position of the RICC assembly 108 in the frame 172, no slack loop of the longitudinal composite 140 remains in the RICC insertion assembly 102, thereby allowing the RICC 106 to continue to advance over the access guidewire 112 with advancement of the longitudinal composite 140.

FIG. 24 provides the RICC insertion assembly 102 with the RICC assembly 108 in the final position in the frame 172 of the RICC insertion device 110 assembly in accordance with some embodiments.

As shown, in the final position of the RICC assembly 108 in the frame 172 of the RICC insertion device 110, the longitudinal composite 140 can be substantially split, the catheter hub 118 of the RICC 106 can lie over the wheel well 180 of the frame 172, and the one-or-more extension legs 120 of the RICC 106 can lie substantially over the handle 176 of the frame 172.

Introducers

FIG. 25 provides the introducer 104 in accordance with some embodiments.

As shown, the introducer 104 can include an introducer needle 214 and a splittable introducer sheath 216. The introducer sheath 216 can be configured to accept therein the introducer needle 214. Indeed, the introducer sheath 216 can be disposed over the introducer needle 214 in a ready-to-operate state of the introducer 104 as shown in FIG. 25. Advantageously, the introducer 104 in combination with the RICC insertion assembly 102 can save a clinician's time in that the introducer needle 214 does not have to be pulled out over the access guidewire 112 and the catheter tube 116 does not have to be threaded over the access guidewire 112.

The introducer needle 214 can include a needle shaft 218 and a needle hub 220. The needle shaft 218 can include a needle tip 222 in a distal portion of the needle shaft 218 configured for establishing a needle tract from an area of skin into a blood-vessel lumen. The needle hub 220 can be coupled to a proximal portion of the needle shaft 218. Advantageously, the introducer needle 214 can be a smaller size than needles typically used to place CVCs, which makes blood-vessel access more convenient. Consequently, the introducer sheath 216 can be configured to not accept therein the catheter tube 116 of the RICC 106.

The introducer sheath 216 can include a splittable sheath body 224 and a splittable sheath hub 226 coupled to a proximal portion of the sheath body 224. Advantageously, the introducer sheath 216 can be configured to split from end to end along a side or a pair of opposing sides of the introducer sheath 216.

The sheath body 224 can be formed of polytetrafluoroethylene, which facilitates smooth, consistent splitting without faults in a side or a pair of opposing sides of the sheath body 224. That said, the sheath body 224 can be formed of any of a number of other polymers (e.g., polyethylene); however, the sheath body 224 can generally benefit by including a single longitudinal fault (e.g., a score, a perforation, etc.) along the side of the sheath body 224 hub or a pair of longitudinal faults including a primary fault and a secondary fault along the pair of opposing sides of the sheath body 224 when formed of the other polymers.

FIG. 26 provides a pair of outwardly extending wings 328 along a length of the sheath hub 226 in accordance with some embodiments.

As shown, the sheath hub 226 can include the wings 328 along a length of the sheath hub 226. The wings 328 can have an internal angle of about 90° or less between the wings 328 configured for splitting the sheath hub 226 by pinching the wings 328 together with a single hand.

The sheath hub 226 can include a single longitudinal fault along a side of the sheath hub 226 or a pair of longitudinal faults including a primary fault and a secondary fault along a pair of opposing sides of the sheath hub 226. When the sheath hub 226 includes the single longitudinal fault, the single longitudinal fault can be along the side of the sheath hub 226 opposite a vertex of the internal angle formed by the wings 328 such that the vertex of the internal angel can function as a living hinge. The sheath hub 226 can be configured to split along the fault for propagation along a same side of the sheath body 224 when the wings 328 are pinched together. When the sheath hub 226 includes the pair of longitudinal faults, the primary fault can extend along a primary side of the sheath hub 226 opposite the vertex of the internal angle formed by the wings 328 and the secondary fault can extend along a secondary side of the sheath hub 226 opposite the primary fault. The sheath hub 226 can be configured to split along the primary fault for propagation along the primary side of the sheath body 224 when the wings 328 are pinched together. The sheath hub 226 can also be configured to split along the secondary fault for propagation along the secondary side of the sheath body 224 when the wings 328 are pulled apart.

FIG. 27 provides a longitudinal cross section of the sheath hub 226 including a valved cap 230 in accordance with some embodiments.

As shown, the sheath hub 226 can include the valved cap 230 disposed in a proximal portion of the sheath hub 226. The valved cap 230 can include a tapered female valved-cap connector 232 and a septum 234 distal of a proximal opening in the female valved-cap connector 232. The female valved-cap connector 232 can be configured to accept therein a tapered male needle-hub connector extending from a distal portion of the needle hub 220. The septum 234 can be configured to accept therethrough the needle shaft 218. Indeed, the male needle-hub connector can be disposed in the female valved-cap connector 232 in the ready-to-operate state of the introducer 104. In addition, the needle shaft 218 can pass through the septum 234 such that the needle tip 222 extends beyond a distal end of the sheath body 224 in the ready-to-operate state of the introducer 104. Notably, the valved cap 230 can be partially or fully split such that the valved cap 230 splits with the sheath hub 226 when the wings 328 are pinched together.

FIGS. 28A and 28B provide an overmolded nicking blade 236 integrated into the sheath hub 226 with a hinged nicking-blade cover 238 respectively in a closed state or safety position and an opened state or nicking position in accordance with some embodiments.

As shown, the sheath hub 226 can include the overmolded nicking blade 236 and the nicking-blade cover 238. The nicking blade 236 can distally extend from the sheath hub 226. When the nicking-blade cover 238 is in the closed state or safety position, the nicking-blade cover 238 can be closed over the nicking blade 236 to prevent inadvertent nicking; however, when the nicking-blade cover 238 is in the opened state or nicking position, the nicking-blade cover 238 can be open away from the nicking blade 236 for nicking an area of skin.

The introducer 104 can further include a syringe 240. The syringe 240 can include a tapered male syringe tip 242 extending from a distal portion of the syringe 240 configured to insert into a tapered female needle-hub connector in a proximal portion of the needle hub 220. The syringe 240 can be configured with a barrel 244 and a plunger 246 to aspirate blood for confirmation of blood-vessel access upon establishing a needle tract from an area of skin into a blood-vessel lumen.

Methods

A method of the RICC insertion system 100 includes a method for inserting the RICC 106 into a blood-vessel lumen of a patient. Such a method includes, in some embodiments, one or more steps selected from an obtaining step, a needle tract-establishing step, a blood-aspirating step, an introducer sheath-advancing step, an introducer needle-removing step, a connector-connecting step, a skin-nicking step, an access guidewire-advancing step, an introducer sheath-removing step, a catheter tube-advancing step, an access guidewire-removing step, a keeper-removing step, a catheter tube-freeing step, a maneuver guidewire-inserting step, a catheter tube-placing step, and a maneuver guidewire-withdrawing step.

The obtaining step can include obtaining the RICC insertion system 100. As set forth above, the RICC insertion system 100 can include the introducer 104, the RICC insertion device 110, and the RICC assembly 108 including the RICC 106. The RICC assembly 108 can be already disposed in the RICC insertion device 110 in the substantially ready-to-operate state of the RICC insertion assembly 102.

The needle tract-establishing step can include establishing a needle tract from an area of skin into the blood-vessel lumen of the patient with the introducer needle 214 of the introducer 104. In addition, the needle tract-establishing step can include ensuring blood flashes back into the needle hub 220 of the introducer needle 214 for confirmation the needle tract extends into the blood-vessel lumen. The introducer needle 214 can be disposed in the introducer sheath 216 of the introducer 104 for the needle tract-establishing step.

The blood-aspirating step can include aspirating blood with the syringe 240 coupled to the introducer needle 214 for confirmation the needle tract extends into the blood-vessel lumen. The blood-aspirating step can be performed before the introducer needle-removing step.

The introducer sheath-advancing step can include advancing the introducer sheath 216 over the introducer needle 214 and farther into the blood-vessel lumen. The introducer sheath-advancing step can be performed before the introducer needle-removing step.

The introducer needle-removing step can include removing the introducer needle 214 from the introducer sheath 216 leaving the introducer sheath 216 in the blood-vessel lumen, thereby allowing the access guidewire 112 to be inserted into the introducer sheath 216.

The connector-connecting step can include inserting the male nose connector 186 of the nose 170 of the RICC insertion device 110 into the female valved-cap connector 232 of the sheath hub 226 of the introducer sheath 216. The connector-connecting step can be performed before the access guidewire-advancing step.

The skin-nicking step can include nicking the area of skin around the needle tract with the nicking blade 236 extending from the sheath hub 226. The skin-nicking step can be performed when the catheter tube 116 is 7 Fr or larger. The skin-nicking step can be accompanied by a cover-opening step before the skin-nicking step and a cover-closing step after the skin-nicking step. The cover-opening step can include opening the nicking-blade cover 238 away from the nicking blade 236 and into the nicking position away from the nicking blade 236. The cover-closing step can include closing the nicking-blade cover 238 over the nicking blade 236 into the safety position over the nicking blade 236. The skin-nicking step can be performed before the access guidewire-advancing step.

The access guidewire-advancing step can include advancing the access guidewire 112 through the nose 170 and nose cover 168 of the RICC insertion device 110, through the sheath hub 226 of the introducer 104, through the introducer sheath 216, and into the blood-vessel lumen. The access guidewire-advancing step can be accomplished, in part, by splitting the splittable casing 136 away from the longitudinal composite 140 of the RICC assembly 108. The distal portion of the access guidewire 112 that extends from the primary-lumen aperture 130 of the catheter tube 116 of the RICC 106 can be freed from the longitudinal composite 140 with the splitting of the splittable casing 136 for the access guidewire-advancing step.

The introducer sheath-removing step can include splitting the introducer sheath 216 to form a split along a side of the introducer sheath 216 by pinching together the wings 328 outwardly extending from the sheath hub 226. The introducer sheath-removing step can also include propagating the split in a side of the sheath hub 226 along a same side of the sheath body 224 of the introducer 104. Ultimately, the introducer sheath-removing step can include removing the split introducer sheath leaving the access guidewire 112 in the blood-vessel lumen.

The skin-nicking step can alternatively include nicking the area of skin around the needle tract with the retractable nicking blade 208 integrated into the nose 170 of the RICC insertion device 110. Such a skin-nicking step is also performed when the catheter tube 116 is 7 Fr or larger. The skin-nicking step can be accompanied by a pair of carriage-sliding steps including a first carriage-sliding step before the skin-nicking step and a second carriage-sliding step after the skin-nicking step. The first carriage-sliding step can include distally sliding the nicking-blade carriage 210 including the nicking blade 208 overmolded therein into the nicking position such that the nicking blade 208 extends beyond the distal end of the nose 170 of the RICC insertion device 110. The second carriage-sliding step can include proximally sliding the nicking-blade carriage into the safety position such that the nicking blade 208 is short of the distal end of the nose 170 of the RICC insertion device 110. The skin-nicking step is also performed before the catheter tube-advancing step.

The catheter tube-advancing step can include advancing the catheter tube 116 over the access guidewire 112 and into the blood-vessel lumen. The catheter tube-advancing step can be accomplished, in part, by further splitting the splittable casing 136 away from the longitudinal composite 140 of the RICC assembly 108. The catheter tube 116 can be freed from the longitudinal composite 140 with the splitting of the splittable casing 136, which allows the catheter tube 116 to be advanced over the access guidewire 112 upon removal of any remaining slack of the longitudinal composite 140 in the RICC insertion assembly 102.

The access guidewire-advancing step or the catheter tube-advancing step set forth above can include repeatedly pushing the longitudinal composite 140 into the one-or-more roller wheels 174 disposed in the wheel well 180 of the handle 176 of the RICC insertion device 110 and rolling the longitudinal composite 140 across the one-or-more roller wheels 174 with a single hand to split the splittable casing away from the longitudinal composite 140. The access guidewire-advancing step or the catheter tube-advancing step can additionally or alternatively include pulling the splittable casing 136 of the longitudinal composite 140 out of the split channel 184 formed between the nose 170 of the RICC insertion device 110 and the nose cover 168 thereover to split the splittable casing away from the longitudinal composite 140.

The access guidewire-removing step can include removing the access guidewire 112 leaving the catheter tube 116 in the blood-vessel lumen.

The keeper-removing step can include removing the keeper 114 including the proximal end of the splittable casing 136 attached to the catheter-hub holder 138 from the RICC assembly 108. The keeper-removing step can be accomplished, in part, by removing the catheter hub 118 of the RICC 106 from the catheter-hub holder 138 and splitting any remaining splittable casing 136 of the longitudinal composite 140 away from the catheter tube 116.

The catheter tube-freeing step can include freeing the catheter tube 116 of the RICC 106 from the retaining clamp 188 formed of the nose 170 and the nose cover 168 of the RICC insertion device 110. The catheter tube-freeing step can be accomplished, in part, by rotating the nose cover 168 over the nose 170 to align the longitudinal gap 190 of the nose cover 168 with the through channel 182 in the nose 170 and pulling the catheter tube 116 away from the RICC insertion device 110. The catheter tube-freeing step can be performed with the keeper-removing step leaving only the RICC 106 with the catheter tube 116 disposed in the blood-vessel lumen.

The maneuver guidewire-inserting step can include inserting a maneuver guidewire into the blood-vessel lumen by way of the distal lumen of the RICC 106. The maneuver guidewire of the maneuver guidewire-advancing step can have a length sufficient for advancing the catheter tube 116 of the RICC 106 to a lower ⅓ of the SVC of a heart of the patient. The maneuver guidewire can be part of a guidewire management device configured to maintain sterility of the maneuver guidewire and facilitate the maneuver guidewire-advancing step. Alternatively, the maneuver guidewire can be a stand-alone maneuver guidewire packaged in a sterile barrier (e.g., a bag, a casing, etc.) configured to maintain sterility of the maneuver guidewire. Such a maneuver guidewire can includes a stopping means to stop advancement of the maneuver guidewire during the maneuver guidewire-advancing step, which obviates losing the maneuver guidewire in the patient. The stopping means can be a ball, a slug, or the like coupled to a proximal portion of the maneuver guidewire configured to not pass through, for example, the Luer connector of the extension leg in which at least the proximal portion of the maneuver guidewire is disposed during the maneuver guidewire-advancing step.

The catheter tube-placing step can include advancing the distal portion of the catheter tube 116 farther into the blood-vessel lumen over the maneuver guidewire to the lower ⅓ of the SVC of the heart of the patient.

The maneuver guidewire-withdrawing step can include withdrawing the maneuver guidewire from the blood-vessel lumen of the patient as well from the RICC 106.

Additional Embodiments

FIGS. 29-31, and 32A-32G provide additional embodiments of RICC insertion systems, RICC insertion kits, components thereof, and associated methods. As noted, for convenience, description for particular components of the RICC insertion systems 100 and 300 is set forth herein in sections but such sections are not intended to limit the description for the particular components of the RICC insertion systems 100 and 300. Indeed, description for any component of the RICC insertion system 100 or 300 can crossover from one section into one or more other sections set forth herein in view of the interrelatedness of the components of the RICC insertion systems 100 and 300.

FIGS. 29-31 provide details of a two-stage RICC insertion system 300 including a RICC insertion assembly 302 having an introducer 304 releasably coupled thereto. As shown in FIG. 29, the RICC insertion assembly 302 can include a RICC insertion device 309 having a housing 310 that defines an interior cavity 312 configured to receive one or more of the RICC 106, the access guidewire 112, optionally, together as the RICC assembly 108 but without the keeper 114, as shown, the introducer 304, a needle-retraction assembly 330, a catheter-advancement assembly 340, and a guidewire-advancement assembly 350 therein. As noted, various embodiments of the RICC assemblies 108, 150, 152, 154, and 158, or the like, can be used with the RICC insertion system 300. Similarly, various embodiments of needle, catheter, or guidewire-advancement assemblies as described herein can be used with the RICC insertion system 300.

An outer surface of the housing 310 can define one or more handles configured to facilitate grasping or manipulating the RICC insertion system 300. For example, the RICC insertion device 309 can include a longitudinal handle 315 and a curved portion 317 defined by the housing 310. Advantageously, the interior cavity 312 of the housing 310 can provide a protective environment within which to receive the RICC assembly 108, allowing a user to manipulate the RICC assembly 108 without having to directly contact the RICC assembly 108 or the RICC 106 or access guidewire 112 thereof. In an embodiment, the RICC insertion device 309 can include one or more flexible barriers. One or both of the housing 310 and the one-or-more flexible barriers can co-operate to maintain the RICC assembly 108 within a sterile environment. In an embodiment, the RICC insertion device 309 can include a blood-flash indicator 321 akin to a barrel of a syringe disposed in the housing 310 in fluid communication with a needle lumen of the introducer needle 314 of the introducer 304, as described in more detail herein.

In an embodiment, one or more of the needle-retraction assembly 330, the catheter-advancement assembly 340, or the guidewire-advancement assembly 350 can be disposed within the interior cavity 312 of the housing 310. As shown, the needle-retraction assembly 330 and the catheter-advancement assembly 340 can be disposed within the longitudinal handle 315. The guidewire-advancement assembly 350 can be disposed within the curved portion 317 of the housing 310. However, other configurations of the needle-retraction assembly 330, the catheter-advancement assembly 340, and the guidewire-advancement assembly 350 are also contemplated.

In an embodiment, the needle-retraction assembly 330 can be configured to transition the introducer needle 314 between an extended position and a retracted position, relative to the housing 310. The needle-retraction assembly 330 can include a needle slider 332, extending through a slot disposed in the housing 310 and slidably engaged therewith. The needle slider 332 can be configured to be manipulated by the user to transition the needle-retraction assembly 330 between the extended position and the retracted position.

In an embodiment, the catheter-advancement assembly 340 can be configured to transition the RICC 106 of the RICC assembly 108 between a retracted position and an extended position, relative to the housing 310. The catheter-advancement assembly 340 can include a catheter slider 342, extending through a slot in the housing 310 and slidably engaged therewith. The catheter slider 342 can be configured to be manipulated by the user to transition the catheter-advancement assembly 340 between the extended position and the retracted position. In an embodiment, the catheter-advancement assembly 340 can engage a portion of the catheter hub 118 of the RICC 106. However, it will be appreciated that the catheter-advancement assembly 340 can engage other portions of the RICC 106 without limitation for transition between the retracted position and the extended position.

In an embodiment, the RICC insertion system 300 can further include the guidewire-advancement assembly 350 including a guidewire slider 352. The guidewire-advancement assembly 350 can be configured to transition the access guidewire 112 between an extended position and a retracted position relative to the housing 310. The guidewire slider 352 can extend through the slot in the housing 310 for manipulation by the user to transition the guidewire-advancement assembly 350 between the retracted position and the extended position.

FIG. 30 provides a detailed view of the introducer 304, which can include an introducer needle 314 supported by a needle hub 320 including a needle lumen, as described herein. The introducer 304 can further include a splittable introducer sheath 316 disposed about a needle shaft of the introducer needle 314 and supported at a proximal end by a splittable sheath hub 326, as described herein. The introducer 304 can further include a nicking blade 308 for nicking skin adjacent an access site to widen the access site and allow the RICC 106 to be advanced into a vasculature.

FIG. 31 provides a detailed view of a nose portion 318 of the RICC insertion device 309 including a blood-flash nozzle 324 and a catheter nozzle 344. A proximal end of the introducer 304 can be configured to releasably engage one or both of the blood-flash nozzle 324 and the catheter nozzle 344 in an interference fit, press fit, or snap fit. In an embodiment, one of the needle hub 320 or the sheath hub 326 can be coupled to either the blood-flash nozzle 324 or the catheter nozzle 344, and the needle hub 320 or the sheath hub 326 can provide fluid communication with one or both of the needle lumen and the sheath lumen. For example, when the introducer 304 is coupled with the blood-flash nozzle 324, the needle lumen can be in fluid communication with the blood-flash indicator 321. A fluid flow can be drawn proximally through the needle lumen and into the blood-flash indicator 321 to observe a color and pulsatile flow to confirm correct vascular access. In an embodiment, the blood-flash indicator 321 can include a vacuum disposed therein, or can be configured to create a vacuum therein, to facilitate drawing a proximal fluid flow.

In an embodiment with the introducer 304 coupled with the blood-flash nozzle 324, a distal portion of the needle-retraction assembly 330 can be coupled with the needle hub 320. Actuating the needle-retraction assembly 330 using the needle slider 332 can withdraw the introducer needle 314 into the housing 310 of the RICC insertion device 309. The sheath hub 326 can then be detached from the blood-flash nozzle 324 and coupled with the catheter nozzle 344 to align the lumen of the introducer sheath 316 with the RICC 106, the access guidewire 112, or both the RICC 106 and the access guidewire 112 of the RICC assembly 108. Advantageously, the introducer needle 314 can be withdrawn into the housing 310 after the vasculature has been accessed and be stored in the housing 310, thereby mitigating accidental needle-stick injuries and exposure of body fluids to the user.

FIGS. 32A-32G provide a different states of the RICC insertion assembly 302 in a method of using the RICC insertion system 300 in accordance with some embodiments. The RICC insertion system 300 can be provided including the introducer 304 coupled to the blood-flash nozzle 324 and the needle-retraction assembly 330 coupled to the needle hub 320. The needle-retraction assembly 330 can be in the extended position with the introducer needle 314 disposed within the lumen of the introducer sheath 316. A distal needle tip of the introducer needle 314 can be disposed distally of the distal tip of the introducer sheath 316. The RICC insertion assembly 302 can further include the RICC 106 coupled to the catheter-advancement assembly 340, the access guidewire 112 coupled to the guidewire-advancement assembly 350, and the RICC assembly 108 including the RICC 106 and the access guidewire 112 disposed within the housing 310 of the RICC insertion device 309. Both the catheter-advancement assembly 340 and the guidewire-advancement assembly 350 can be in a retracted position with a distal tip of the RICC 106 and a distal tip of the access guidewire 112 disposed within the housing 310.

The user can access a vasculature of the patient by grasping one of the longitudinal handle 315 or the curved portion 317 of the housing 310 to manipulate the RICC insertion assembly 302 and urge the introducer needle 314 distally into the vasculature. As such, the introducer needle 314 and introducer sheath 316 assembly can simultaneously access the vasculature. The blood-flash indicator 321 can draw a fluid flow proximally through the needle lumen and into the blood-flash indicator 321 to confirm correct vascular access.

As shown in FIGS. 32A and 32B, once correct vascular access is confirmed the user can actuate the needle slider 332 to transition the needle-retraction assembly 330 to the retracted position (FIG. 32B) and withdraw the introducer needle 314 from the introducer sheath 316, securing the introducer needle 314 within the housing 310 of the RICC insertion device 309. In an embodiment, the RICC insertion device 309 can then be detached from the introducer 304, or more specifically detached from the sheath hub 326, leaving the introducer sheath 316 in place within the vasculature to maintain patency of the access site. In an embodiment, the user can grasp the sheath hub 326 and advance the introducer sheath 316 further into the access site. The nicking blade 308 disposed proximate the sheath hub 326 can nick the skin adjacent the access site to widen the access site and allow the RICC 106 to be advanced into the vasculature.

Advantageously, detaching the RICC insertion device 309 from the sheath hub 326 allows the user to maintain patency of the access site without having to stabilize the RICC insertion assembly 302 (sans the introducer 104), and any associated components, adjacent the access site. For example, the user can pause the catheter-placement process to prepare subsequent steps, or the like, without having to restart the entire placement process. Further, the blood-flash indicator 321, the introducer needle 314, and the needle-retraction assembly 330 can be off-set from an axis of the catheter-advancement assembly 340, the guidewire-advancement assembly 350, or both, thereby allowing for unobstructed travel of the RICC 106 and the access guidewire 112, as described herein.

As shown in FIG. 32C, the user can couple the catheter nozzle 344 with the sheath hub 326 to continue the catheter-placement process. Coupling the sheath hub 326 with the catheter nozzle 344 aligns a sheath lumen with the RICC 106, the access guidewire 112, or both. As shown in FIG. 32D, the user can then actuate the guidewire-advancement assembly 350, by manipulating the guidewire slider 352, to transition the access guidewire 112 from the retracted position (FIG. 32C) to the extended position (FIG. 32D). In the extended position, the distal tip of the access guidewire 112 can extend through the primary lumen 124 of the RICC 106, through the catheter nozzle 344 of the housing 310, through the lumen of the introducer sheath 316, and into the vasculature of the patient, until the distal tip of the access guidewire 112 is positioned at a target location.

As shown in FIG. 32E, the user can then split the introducer sheath 316 longitudinally into a first portion 316A and a second portion 316B. The user can grasp the wings 328 of the sheath hub 326 and urge them apart laterally to split the sheath hub 326 and the introducer sheath 316. The sheath portions 316A and 316B can then be withdrawn proximally from the access site while the access guidewire 112 maintains patency of the access site. Advantageously, since the inner diameter of the lumen of the introducer sheath 316 is less than an outer diameter of the catheter tube 116 or the RICC 106, the introducer sheath 316 can be split and removed to allow the RICC 106 to be advanced over the access guidewire 112 and into the vasculature.

As shown in FIG. 32F, the user can then actuate the catheter slider 342 to transition the catheter-advancement assembly 340 from the retracted position to the extended position. In the extended position, the RICC 106 can be advanced over the access guidewire 112 and into the vasculature. In an embodiment, the housing 310 can include a first lateral slot 360A and a second lateral slot 360B disposed opposite the first lateral slot across a central longitudinal axis of the catheter nozzle 344 (FIG. 31). The first lateral slot 360A and the second lateral slot 360B can extend longitudinally proximally from a distal tip of the catheter nozzle 344 and can communicate with the interior cavity 312 of the housing 310. As such, the first lateral slot 360A and the second lateral slot 360B can allow the catheter hub 118, and the one-or-more extension legs 120 to pass therethrough, allowing the RICC 106 to disengage the housing 310, once placed. As show in FIG. 32G, the guidewire slider 352 can then be retracted to transition the guidewire-advancement assembly 350 and the access guidewire 112 to the retracted position, storing the access guidewire 112 within the housing 310 and mitigating exposure of body fluids to the user.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A rapidly insertable central catheter ("RICC") insertion system, comprising:
    a RICC assembly including:
        a RICC including:
            a catheter tube;
            a catheter hub coupled to a proximal portion of the catheter tube; and
            one or more extension legs, each extension leg of the one or more extension legs coupled to the catheter hub by a distal portion thereof;
        an access guidewire disposed in a primary lumen of the RICC; and
        a keeper including a splittable casing over both the catheter tube and a distal portion of the access guidewire extending from a distal end of the RICC forming a longitudinal composite thereof;
    a RICC insertion device including:
        a frame including:
            a longitudinal handle including a wheel well;
            a nose extending from a distal portion of the longitudinal handle, distal of the wheel well, the nose including a through channel configured for advancing the catheter tube of the RICC therethrough; and
            a curved cradle extending from a proximal portion of the longitudinal handle;
        one or more roller wheels disposed in the wheel well; and
        a nose cover over the nose, the nose cover and the nose forming a split channel configured for both splitting and passing the splittable casing therethrough, the RICC insertion device configured for advancing the RICC assembly from an initial position in the frame to a final position in the frame by repeatedly pushing the longitudinal composite into the one or more roller wheels and rolling the longitudinal composite across the one or more roller wheels; and
    an introducer.

2. The RICC insertion system of claim 1, wherein the keeper further includes a catheter-hub holder to which a proximal end of the splittable casing is attached, the catheter-hub holder configured to hold the catheter hub therein and keep the splittable casing in position over the catheter tube and the access guidewire.

3. The RICC insertion system of claim 2, wherein the catheter-hub holder includes a perimetrical wall around at least a portion of a perimeter of the catheter-hub holder, the perimetrical wall defining a recess into which the catheter hub fits with an engineering fit.

4. The RICC insertion system of claim 1, wherein the curved cradle includes a curved extension over a distal portion of the curved cradle, the curved extension following a same curve as the curved cradle.

5. The RICC insertion system of claim 4, wherein the curved cradle includes an enclosure over the distal portion of the curved cradle with the curved extension extending therefrom, the enclosure configured to enclose therein an otherwise exposed proximal portion of the access guidewire in the initial position of the RICC assembly in the frame.

6. The RICC insertion system of claim 4, further comprising a retaining clip configured to clip on to a proximal portion of the RICC, retain the RICC assembly in the RICC insertion device, and keep the catheter tube from prematurely advancing over the access guidewire, the retaining clip including a post configured to engage with a slot in the curved extension that faces an open face of the curved cradle.

7. The RICC insertion system of claim 6, wherein the retaining clip is configured to disengage with the slot in the curved extension when any remaining slack of the longitudinal composite is removed upon advancing the RICC assembly from the initial position to the final position in the frame.

8. The RICC insertion system of claim 1, the frame further including a retaining arch over the curved cradle proximate the proximal portion of the longitudinal handle from which the curved cradle extends, the retaining arch configured to retain the RICC assembly in the RICC insertion device and hold the longitudinal composite over the longitudinal handle as the RICC assembly transitions over the proximal portion of the longitudinal handle from which the curved cradle extends upon advancing the RICC assembly from the initial position to the final position in the frame.

9. The RICC insertion system of claim 1, wherein the nose cover and the nose further form a retaining clamp configured to slidably clamp the longitudinal composite therein, the nose cover rotatable over the nose, and the nose cover including a longitudinal gap configured to rotatably align with the through channel in the nose for removal of the longitudinal composite, the splittable casing, or the catheter tube therefrom.

10. The RICC insertion system of claim 1, further comprising a retractable nicking blade, the retractable nicking blade disposed in a nicking-blade carriage slidably integrated into the nose, the nicking-blade carriage having a nicking position with the retractable nicking blade extending beyond a distal end of the nose and a safety position with the retractable nicking blade short of the distal end of the nose.

11. The RICC insertion system of claim 1, the introducer including:
an introducer needle including:
a needle shaft including a needle tip in a distal portion of the needle shaft; and
a needle hub coupled to a proximal portion of the needle shaft; and
a splittable introducer sheath configured to accept therein the introducer needle,
the splittable introducer sheath including:
a splittable sheath body; and
a splittable sheath hub coupled to a proximal portion of the splittable sheath body, the splittable sheath hub including a pair of outwardly extending wings along a length of the splittable sheath hub having an internal angle of about 90° or less between the outwardly extending wings configured for splitting the splittable sheath hub by pinching the outwardly extending wings together with a single hand.

12. The RICC insertion system of claim 11, wherein the splittable sheath hub includes a single longitudinal fault along a side of the splittable sheath hub opposite a vertex of the internal angle formed by the outwardly extending wings, the splittable sheath hub configured to split along the single longitudinal fault for propagation along a same side of the splittable sheath body when the outwardly extending wings are pinched together.

13. The RICC insertion system of claim 11, wherein the splittable sheath hub includes a pair of longitudinal faults including a primary fault along a primary side of the splittable sheath hub opposite a vertex of the internal angle formed by the outwardly extending wings and a secondary fault along a secondary side of the splittable sheath hub opposite the primary fault, the splittable sheath hub configured to split along the primary fault for propagation along the primary side of the splittable sheath body when the outwardly extending wings are pinched together, and the splittable sheath hub configured to split along the secondary fault for propagation along the secondary side of the splittable sheath body when the outwardly extending wings are pulled apart.

14. The RICC insertion system of claim 11, the splittable sheath hub further including a valved cap disposed in a proximal portion of the splittable sheath hub, the valved cap including a tapered female valved-cap connector and a septum, distal of a proximal opening in the tapered female valved-cap connector, the tapered female valved-cap connector configured to accept therein a tapered male needle-hub connector extending from a distal portion of the needle hub, and the septum configured to accept therethrough the needle shaft.

15. The RICC insertion system of claim 14, wherein the valved cap is partially or fully split such that the valved cap splits with the splittable sheath hub when the outwardly extending wings are pinched together.

16. The RICC insertion system of claim 11, the splittable sheath hub further including:
an overmolded nicking blade distally extending from the splittable sheath hub; and
a hinged nicking-blade cover having an opened state with the hinged nicking-blade cover opened away from the overmolded nicking blade and a closed state with the hinged nicking-blade cover closed over the overmolded nicking blade.

17. The RICC insertion system of claim 11, further comprising a syringe including a tapered male syringe tip extending from a distal portion of the syringe, the tapered male syringe tip configured to insert into a tapered female needle-hub connector in a proximal portion of the needle hub.

18. A rapidly insertable central catheter ("RICC") insertion assembly, comprising:
a RICC assembly including:
a RICC including:
a catheter tube;
a catheter hub coupled to a proximal portion of the catheter tube; and
one or more extension legs, each extension leg of the one or more extension legs coupled to the catheter hub by a distal portion thereof;
an access guidewire disposed in a primary lumen of the RICC; and
a keeper including a splittable casing over both the catheter tube and a distal portion of the access guidewire extending from a distal end of the RICC forming a longitudinal composite thereof; and
a RICC insertion device including:
a frame including:
a longitudinal handle including a wheel well;
a nose extending from a distal portion of the longitudinal handle, distal of the wheel well, the nose including a through channel configured for advancing the catheter tube of the RICC therethrough; and
a curved cradle extending from a proximal portion of the longitudinal handle;
one or more roller wheels disposed in the wheel well; and
a nose cover over the nose, the nose cover and the nose forming a split channel configured for both splitting and passing the splittable casing therethrough, the RICC insertion device is configured for advancing the RICC assembly from an initial position in the frame to a final position in the frame by repeatedly pushing the longitudinal composite into the one or more roller wheels and rolling the longitudinal composite across the one or more roller wheels.

19. The RICC insertion assembly of claim 18, wherein a distal end of the longitudinal composite, the splittable casing, or the access guidewire is commensurate with a distal end of the frame in the initial position of the RICC assembly in the frame.

20. The RICC insertion assembly of claim 18, wherein a slack loop of the longitudinal composite extends away from both the longitudinal handle and the curved cradle in the initial position of the RICC assembly in the frame.

21. The RICC insertion assembly of claim 18, wherein the longitudinal composite is split in the final position of the RICC assembly in the frame.

22. The RICC insertion assembly of claim 18, wherein a proximal end of an extension leg or a Luer connector coupled to the extension leg of the one or more extension legs of the RICC is commensurate with a proximal end of the curved cradle in the initial position of the RICC assembly in the frame.

23. The RICC insertion assembly of claim 22, wherein a proximal end of the access guidewire is coupled to the proximal end of the curved cradle in the initial position of the RICC assembly in the frame.

24. The RICC insertion assembly of claim 22, wherein the one or more extension legs of the RICC lie over the longitudinal handle in the final position of the RICC assembly in the frame.

25. The RICC insertion assembly of claim 18, wherein the catheter hub of the RICC lies over the wheel well in the final position of the RICC assembly in the frame.

* * * * *